US012797039B2

(12) United States Patent
Zhou

(10) Patent No.: US 12,797,039 B2
(45) Date of Patent: Nov. 17, 2026

(54) ADJUSTABLE PATCH FOR SECURING ULTRASONIC TRANSDUCERS

(71) Applicant: Circucare Inc., San Diego, CA (US)

(72) Inventor: Sai Zhou, San Diego, CA (US)

(73) Assignee: Circucare Inc., San Diego, CA (US)

( * ) Notice: Subject to any disclaimer, the term of this patent is extended or adjusted under 35 U.S.C. 154(b) by 0 days.

(21) Appl. No.: 19/351,031

(22) Filed: Oct. 6, 2025

(65) Prior Publication Data

US 2026/0096805 A1 Apr. 9, 2026

Related U.S. Application Data

(60) Provisional application No. 63/802,337, filed on May 8, 2025, provisional application No. 63/703,984, filed (Continued)

(51) Int. Cl.
*A61B 8/00* (2006.01)
*A61B 8/14* (2006.01)
(Continued)

(52) U.S. Cl.
CPC .............. *A61B 8/4236* (2013.01); *A61B 8/14* (2013.01); *A61B 8/4227* (2013.01); (Continued)

(58) Field of Classification Search
CPC ....... A61B 8/4236; A61B 8/14; A61B 8/4227; A61B 8/4272; A61B 8/4281; A61B 8/4427; A61B 8/4455; A61B 8/4472; A61B 8/4477; A61B 8/4488; A61B 8/4494; A61B 8/462; A61B 8/54; A61B 8/56; A61B 90/08; A61B 2090/0807; A61B 2560/0214; A61B 2560/0462; A61B 2562/0204; A61B 2562/043; A61B 2562/046; A61B 2562/166; A61B 2562/227; A61B 8/4483;
(Continued)

(56) References Cited

U.S. PATENT DOCUMENTS 3,299,882 A * 1/1967 Masino .................. A61B 5/021
600/398
4,920,966 A 5/1990 Hon et al.
(Continued)

FOREIGN PATENT DOCUMENTS

WO WO 2023246426 A1 12/2023

OTHER PUBLICATIONS

International Search Report and Written Opinion in International Appln. No. PCT/US2025/049697, mailed on Jan. 30, 2026, 14 pages.
(Continued)

*Primary Examiner* — Bo Joseph Peng
(74) *Attorney, Agent, or Firm* — Fish & Richardson P.C.

(57) ABSTRACT

A wearable ultrasound system includes an ultrathin ultrasound device comprising an array of piezoelectric elements disposed on a backing layer and coupled to a flexible printed circuit board (FPCB); an adjustable patch attachable to a region of a subject, the adjustable patch operably holds the ultrathin ultrasound device therein so that the ultrathin ultrasound device is adjustably coupled to the region of the subject through coupling fluid in the adjustable patch; and a portable control system communicatively coupled to the ultrathin ultrasound device.

5 Claims, 15 Drawing Sheets

Related U.S. Application Data on Oct. 6, 2024, provisional application No. 63/703,982, filed on Oct. 6, 2024, provisional application No. 63/703,985, filed on Oct. 6, 2024.

(51) Int. Cl.

| | |
|---|---|
| ***A61B 90/00*** | (2016.01) |
| ***B06B 1/06*** | (2006.01) |

(52) U.S. Cl.

CPC .......... *A61B 8/4272* (2013.01); *A61B 8/4281* (2013.01); *A61B 8/4427* (2013.01); *A61B 8/4455* (2013.01); *A61B 8/4472* (2013.01); *A61B 8/4477* (2013.01); *A61B 8/4488* (2013.01); *A61B 8/4494* (2013.01); *A61B 8/462* (2013.01); *A61B 8/54* (2013.01); *A61B 8/56* (2013.01); *A61B 90/08* (2016.02); *B06B 1/0629* (2013.01); *A61B 2090/0807* (2016.02); *A61B 2560/0214* (2013.01); *A61B 2560/0462* (2013.01); *A61B 2562/0204* (2013.01); *A61B 2562/043* (2013.01); *A61B 2562/046* (2013.01); *A61B 2562/166* (2013.01); *A61B 2562/227* (2013.01); *B06B 2201/76* (2013.01)

(58) Field of Classification Search

CPC .. A61B 8/4444; B06B 1/0629; B06B 2201/76
See application file for complete search history.

(56) References Cited

U.S. PATENT DOCUMENTS

| | | | | |
|---|---|---|---|---|
| 8,414,495 | B2 | 4/2013 | Halmann et al. | |
| 2011/0087107 | A1* | 4/2011 | Lindekugel .......... | A61B 8/4455<br>600/459 |
| 2016/0302766 | A1* | 10/2016 | Liu ...................... | A61B 8/4236 |
| 2017/0205318 | A1* | 7/2017 | Matula .................. | B06B 1/0215 |
| 2018/0021014 | A1* | 1/2018 | Chen ........................ | A61B 8/56<br>600/459 |
| 2019/0374198 | A1* | 12/2019 | Mullen ................ | A61B 8/4422 |
| 2020/0383660 | A1 | 12/2020 | Rothberg et al. | |
| 2022/0401066 | A1 | 12/2022 | Verbakel et al. | |
| 2023/0355204 | A1 | 11/2023 | Xu et al. | |

OTHER PUBLICATIONS

Zhou et al., "Transcranial Volumetric Imaging Using a Conformal Ultrasound Patch," Nature, May 22, 2024, 629:810-818.

* cited by examiner

ADJUSTABLE PATCH FOR SECURING ULTRASONIC TRANSDUCERS

CROSS-REFERENCE TO RELATED APPLICATIONS

This application claims the benefit of U.S. Provisional Application No. 63/703,982, filed Oct. 6, 2024, U.S. Provisional Application No. 63/703,984, filed Oct. 6, 2024, U.S. Provisional Application No. 63/703,985, filed Oct. 6, 2024, and U.S. Provisional Application No. 63/802,337, filed May 8, 2025, the contents of which are incorporated by reference herein.

TECHNICAL FIELD

The present disclosure relates generally to medical imaging, including medical imaging devices and systems, such as a wearable imaging system and components thereof and a wearable system, e.g., that can enable hands-free, continuous, multi-angle, and multi-target imaging of internal targets.

BACKGROUND

An ultrasound imaging system is widely used as a non-invasive diagnostic tool in medical imaging. An exemplary ultrasound imaging system operates by transmitting high-frequency (e.g., in the megahertz range) ultrasound waves into the body using a transducer or a transducer array, and then capturing the echoes that bounce back from tissues and organs. These echoes are converted into electrical signals and then processed to create real-time images depicting the tissues and organs, known as sonograms.

SUMMARY

A wearable ultrasound system is disclosed that features: an ultrathin ultrasound device comprising an array of piezoelectric elements disposed on a backing layer and coupled to a flexible printed circuit board (FPCB); an adjustable patch attachable to a region of a subject, the adjustable patch operably holds the ultrathin ultrasound device therein so that the ultrathin ultrasound device is adjustably coupled to the region of the subject through coupling fluid in the adjustable patch; and a portable control system communicatively coupled to the ultrathin ultrasound device, the portable control system comprising one or more circuits configured to: control the ultrathin ultrasound device to emit ultrasound waves into the region of the subject, and receive echoes from the region of the subject in response to the ultrasound waves; receive electrical signals from the ultrathin ultrasound device when the echoes are received by the ultrathin ultrasound device; and generate one or more diagnostic images or waveforms based on the electrical signals.

In some implementations, the ultrathin ultrasound device includes: an ultrasonic transducer array that includes a plurality of elements each comprising a back electrode and a front electrode, and configured to: generate ultrasound waves for launching from a front surface into a region of a subject, and receive echoes from the region in response to the ultrasonic waves being launched from the front surface, the front surface encompassing the front electrode; a backing layer positioned at a back surface of the ultrasonic transducer array and configured to absorb the ultrasonic waves generated by the ultrasonic transducer array that otherwise would be launched from the back surface, the back surface encompassing the back electrode and the front electrode expands from the ground surface through the side face of the transducer; and a flexible printed circuit board (FPCB) comprising electrical wiring routed to electrically connect the front electrode and the back electrode of each of the plurality of elements of the ultrasonic transducer array so that the plurality of elements can generate the ultrasound waves when driven by electrical pulses and generate electrical signals when the echoes are received, wherein the ultrathin ultrasound device is sized five millimeters or less in thickness.

In some implementations, the adjustable patch includes: a mounting plate integrated with a gel sprue, the mounting plate sized and shaped to hold an ultrasonic transducer array, the gel sprue constructed to allow replenishment of coupling gel for the ultrasonic transducer array; and an adjustment base disposed underneath the mounting plate, the adjustment base including a clip configured to grip the mounting plate, wherein the clip is coupled with an adjustment knob operable to tighten or loosen the clip so that the ultrasonic transducer array in the mounting plate can be securely attached to, or detached from, a subject's skin, wherein the adjustable patch is attachable to the subject's skin using one or more breathable medical tapes.

In one aspect, some implementations provide a band system for affixing one or more wearable ultrasound devices, the band system including: one or more mounts, wherein each mount is defined by a horizontal plane and a longitudinal axis that is vertical to the horizontal plane, wherein each mount encloses a respective knob operable to rotate around the longitudinal axis and tilt about the horizontal plane; and straps tied to the one or more mounts, wherein the straps are adjustable to wrap around a subject so that the subject can wear the one or more mounts, wherein each mount houses a wearable ultrasound device such that, by virtue of wearing the one or more mounts, each wearable ultrasound device is placed with sufficient acoustic coupling with the subject's skin.

Some implementations may include one or more of the following features.

Each mount may be embedded with markings to respectively indicate a degree of rotation and an angle for tilt, wherein the markings are provided in a first number of intervals for rotational degrees and a second number of intervals for tilting angles. Each wearable ultrasound device may be sized and shaped for attachment to a corresponding knob. Each wearable ultrasound device, when placed in sufficient contact with the subject's skin, may provide a separate view of an internal region of the subject. The internal region may include at least one of: a heart region, an abdominal region, a neck region, a joint region, an extremity region, a lung region, and a head region. A composite view of the internal region may be generated based on the separate views from respective wearable ultrasound devices. Each wearable ultrasound device may be coupled to a control system configured to drive each wearable ultrasound device for imaging the internal region of the subject. The control system may include at least one of: a matching and tuning element, an amplifier circuit, and a beamformer. The band system may further include: an electrical interface connecting the ultrasound device to the control system. The control system may have a form factor sufficiently small for fitting on a mount or a knob. The band system may further include: a locking mechanism on each mount and operable to lock the respective knob enclosed therein so that an orientation of the ultrasound device with respect to the subject's skin is fixed. The locking mechanism may include: a nut coupled to the mount for regulating tension on the straps tied to the mount; and a latch toggleable between a first position to fix an orientation of the knob, and a second position to release the orientation of the knob. Each mount and the straps may be composed of biocompatible materials designed for prolonged skin contact and comfort. The wearable ultrasound device housed within the mount may include at least one of: a phased array, a linear array, a curved array, a matrix array, or a reconfigurable array. The band system may further include one or more actuating devices arranged on one of the mount or the knob, wherein the one or more actuating devices are configured to rotate the knob around the longitudinal axis and tilt the knob about the horizontal plane.

The details of one or more implementations of the subject matter of this specification are set forth in the Detailed Description, the accompanying drawings, and the claims. Other features, aspects, and advantages of the subject matter will become apparent from the Detailed Description, the claims, and the accompanying drawings.

BRIEF DESCRIPTION OF DRAWINGS

Like reference numbers and designations in the various drawings indicate like elements.

DETAILED DESCRIPTION

Figure 1:
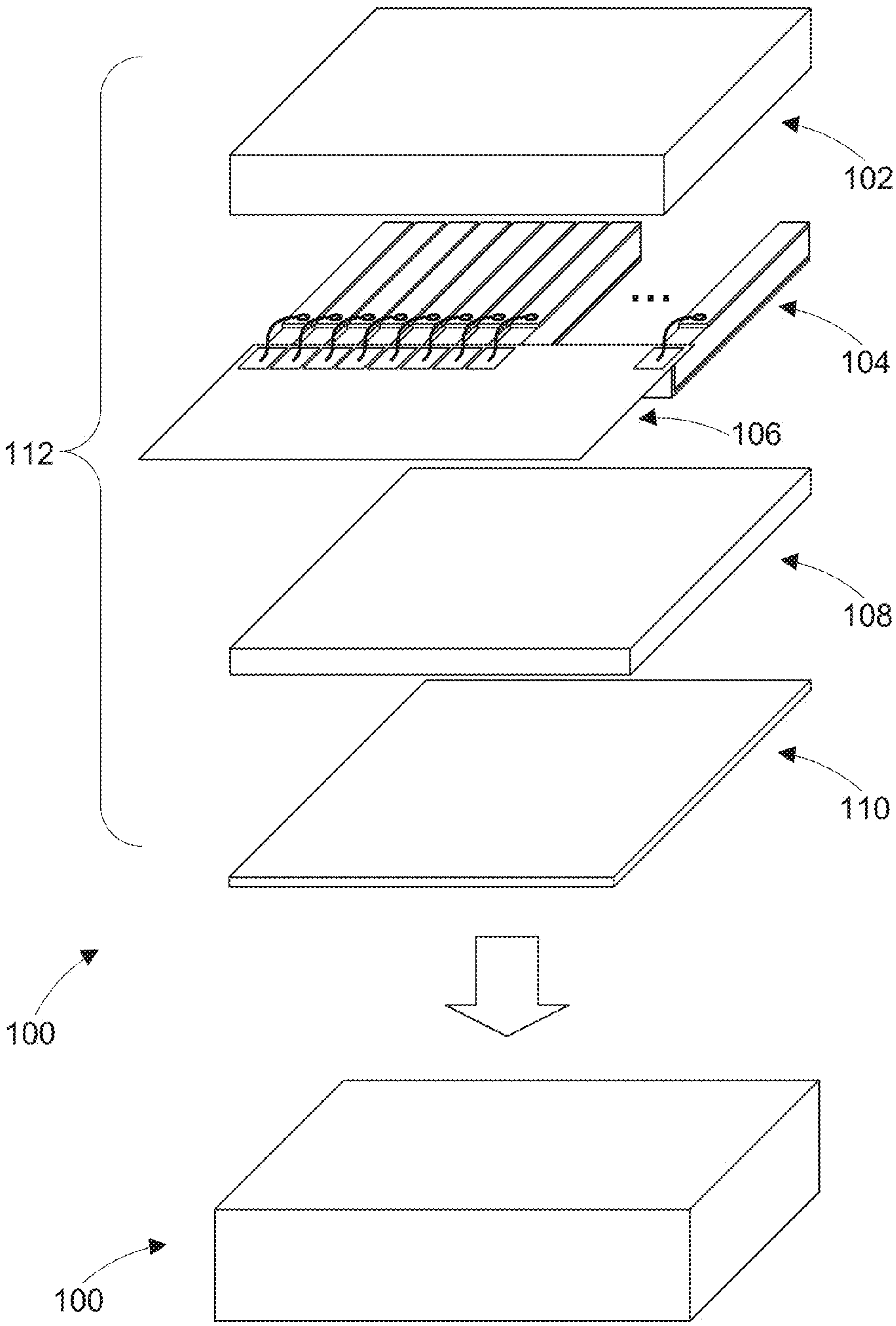
FIG. 1 illustrates an ultrathin ultrasound device according to some implementations of the present disclosure.

The detailed description explains a wearable ultrasound system that includes an ultrathin ultrasonic transducer device designed to overcome the limitations of traditional transducer designs and an adjustable patch for securing the ultrathin ultrasonic transducer device to a region of a subject for long-term monitoring. Various modifications, alterations, and permutations of the disclosed implementations can be made and will be readily apparent to those of ordinary skill in the art, and the general principles defined may be applied to other implementations and applications, without departing from the scope of the disclosure. In some instances, details unnecessary to obtain an understanding of the described subject matter may be omitted so as to not obscure one or more described implementations with unnecessary detail and inasmuch as such details are within the skill of one of ordinary skill in the art. The present disclosure is not intended to be limited to the described or illustrated implementations, but to be accorded the widest scope consistent with the described principles and features.

Ultrathin Ultrasonic Transducer Array

The present disclosure describes an ultrathin ultrasonic transducer device including a transducer array with enhanced acoustic performance. As explained in more detail with reference to FIGS. 1 and 2A to 2D, the ultrathin ultrasonic transducer device can include a backing layer, an ultrasonic transducer array, a flexible printed circuit board (FPCB) with a reduced footprint, one or more matching layers, and an acoustic lens. The ultrathin ultrasonic transducer device can have an overall thickness of less than 5 millimeters (mm), for example. Each constituent layer of the ultrathin ultrasonic transducer device can be closely adhered to the next. The FPCB can be connected to the back electrode of each element of the ultrasonic transducer array through wire bonding. By reducing the coverage area of the FPCB over the ultrasonic transducer array, the obstruction caused by the metal layers of the FPCB can be reduced so that the absorption effect of the acoustic backing layer can be enhanced to reduce background noise, thereby improving the overall acoustic performance. The ultrathin ultrasound transducer device can be compact, lightweight, and suitable for wearable applications, such as continuous medical monitoring and point-of-care diagnostics, which are applicable to not only long-term care facilities, but also at home monitoring scenarios.

For context, ultrasonic transducers used in medical imaging are typically composed of several layers, including a backing layer, a piezoelectric transducer array, one or more matching layers, and an acoustic lens, each playing an integral role in achieving high efficiency and quality of ultrasound imaging. One challenge of ultrasonic transducer construction lies in the design and integration of a flexible printed circuit board, also known as the FPCB. The FPCB, often used to connect the transducer array to external electronics, can cover a significant portion of the transducer area. This extensive coverage can significantly obstruct the propagation of ultrasound waves due to the metal layers of the FPCB, which creates impedance mismatches and interferes with acoustic signals to reduce the overall efficiency of ultrasound absorption by the backing layer.

To compensate for limitations in conventional designs of traditional ultrasonic transducers used in medical imaging, the backing layer can be made relatively thick—typically around 5 to 10 mm. Such a backing layer with increased thickness can enhance ultrasound absorption performance and reduce unwanted reflections (e.g., from the back surface of the ultrasonic transducer array), which can degrade image quality. However, this increased thickness can result in a bulky ultrasound device unsuitable for applications demanding compactness and portability such as wearable devices. Moreover, the bulky design can hinder the integration of ultrasound technology into emerging applications such as continuous patient monitoring, telemedicine, and home healthcare, where device size and comfort may be paramount.

Implementations of the present disclosure can overcome the above-discussed issues by improving the design and integration of the FPCB and enhancing the overall transducer structure. By reducing the coverage area of the FPCB over the ultrasonic transducer array and reducing the obstruction from the metal layers, the design can include a much thinner backing layer while maintaining effective ultrasound absorption. Additionally, advanced materials and fabrication techniques can be employed to enhance acoustic performance. The implementations can result in an overall device thickness of less than 5 mm, making the design highly suitable for wearable applications.

Some implementations incorporate an ultrathin wearable ultrasonic transducer device designed to overcome the limitations of traditional transducer designs. The ultrathin wearable ultrasonic transducer device can include an improved backing layer composed of an epoxy resin mixed with high-density metal or ceramic-based materials, such as tungsten powder, silver powder, alumina powder, or carbon fiber. The backing layer can effectively absorb unwanted acoustic waves while maintaining minimal thickness.

In some implementations, the ultrathin wearable ultrasonic transducer device can include an ultrasonic transducer array made from advanced piezoelectric materials such as single crystals, composite materials, or lead zirconate titanate (PZT) ceramics. These materials can offer high electromechanical coupling coefficients and bandwidth, enhancing imaging performance.

In some implementations, a FPCB with significantly reduced footprint can be connected to the ultrasonic transducer array using conductive epoxy bonding or soldering. Specifically, the conductive wires on the FPCB can be wire-bonded to the transducer array using gold wires, which can significantly improve connectivity while reducing the FPCB's physical footprint over the transducer array, thereby significantly reducing, and potentially minimizing, acoustic obstruction.

In some implementations, one or more matching layers can improve the efficient transmission of ultrasonic waves by significantly improving impedance matching between the transducer array and the acoustic lens. An acoustic lens, possibly made of silicone rubber or other suitable materials, can focus the ultrasonic waves, enhancing imaging resolution and depth of field.

The implementations can result in a total thickness of less than 5 mm, making the device lightweight, highly portable, and suitable for wearable applications. The design can reduce noise, enhance the quality of ultrasound imaging, and enable integration into a variety of medical and industrial applications that require compact ultrasound solutions.

FIG. 1 is an exploded view of the ultrathin ultrasound device 100 including a backing layer 102, an ultrasonic transducer array 104, an FPCB 106, matching layer(s) 108, and an acoustic lens 110. In some implementations, an overall thickness 112 can be less than five millimeters (5 mm).

As illustrated, the ultrasonic transducer array 104 includes a plurality of elements (also known as transducer elements). Each element includes a back electrode and a front electrode. The ultrasonic transducer array 104 is configured to generate ultrasound waves for launching from a front surface into a region of a subject (e.g., a target region inside the subject), and receive echoes from the region in response to the ultrasonic waves being launched from the front surface. The front surface encompasses the front electrode. The backing layer 102 is positioned at the back surface of the ultrasonic transducer array and configured to absorb, e.g., the ultrasonic waves generated by the ultrasonic transducer array that otherwise would be launched from the back surface. The back surface encompasses the back electrode while the front electrode expands from the ground surface through the side face of the transducer. The FPCB includes electrical wiring routed to electrically connect the front electrode and the back electrode of each of the plurality of elements of the ultrasonic transducer array. As such, the plurality of elements can generate ultrasound waves when driven by electrical pulses and generate electrical signals when the echoes are received. The ultrathin ultrasound device is sized, for example, five millimeters or less in thickness.

FIGS. 2A-2D illustrate an assembly process for an ultrasonic transducer array 200, which can operate as the ultrasonic transducer array 104 as part of the ultrathin ultrasound device 100 of FIG. 1.

Figure 2A:
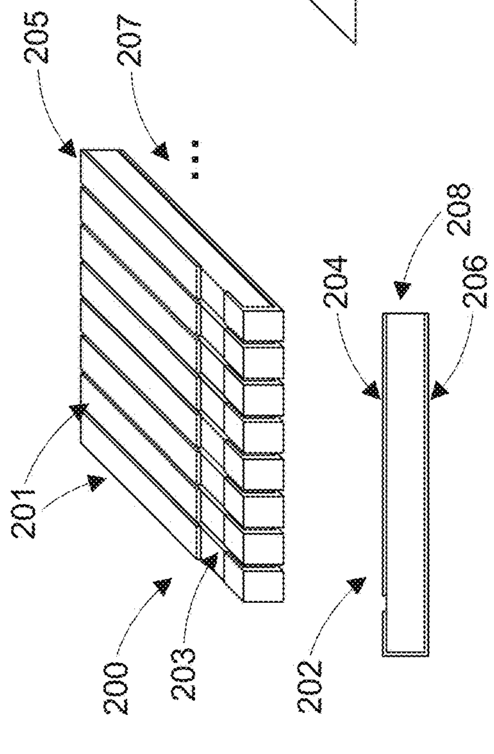
FIGS. 2A-2D illustrate an assembly process for an ultrasonic transducer array according to some implementations of the present disclosure.

FIG. 2A shows the ultrasonic transducer array 200 as a plurality of bar-shaped elements 201 disposed in parallel. As revealed in the side view 202, each bar-shaped element 201 is made from single-crystal material, composites, or PZT ceramics 208. Each bar-shaped element 201 includes a back electrode 204 covering a major portion of the back surface 205, and a front electrode 206 covering the front surface 207 and wrapping around to cover an edge of the back surface 205. The back electrode 204 and the front electrode 206 are separated, as indicated by a region 203.

Figure 2B:
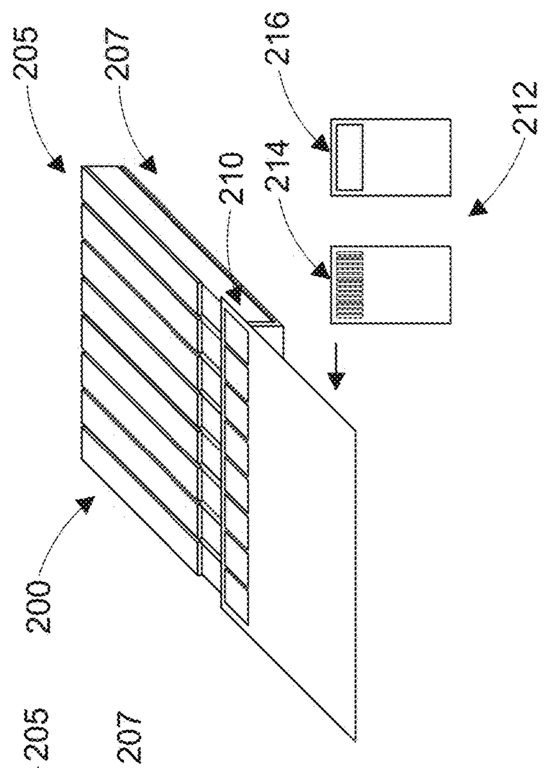

FIG. 2B shows an attachment of an FPCB 212 to the front electrode 206 (configured as the ground electrode) of each bar-shaped element 201 of the ultrasonic transducer array 200 through conductive epoxy bonding or soldering 210. As the ground electrode, the front electrode 206 of all bar-shaped elements 201 of the ultrasonic transducer array 200 is connected to the contiguous bar on the front side of FPCB 212, as revealed in front view 214 of FPCB 212. The back electrode 204 of each bar-shaped element of the ultrasonic transducer array 200 is connected to a corresponding connection spot on the back side of FPCB 212, as revealed in back view 216 of FPCB 212. The FPCB 212 can correspond to the FPCB 106 of FIG. 1

Figure 2C:
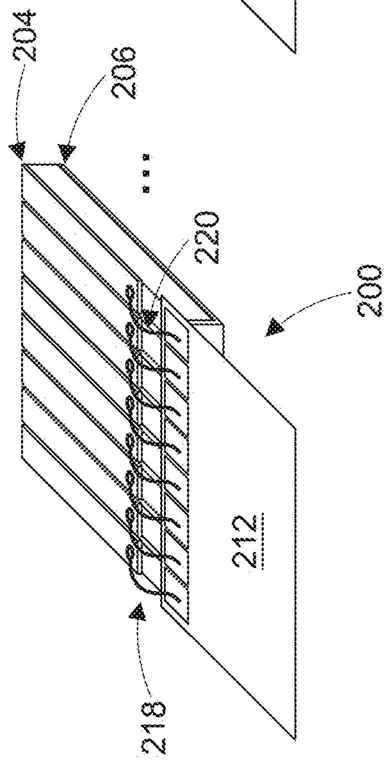

FIG. 2C shows a wire bonding 218 connection between each corresponding connection spot on the back side of FPCB 212 to each back electrode 204 of bar-shape elements 201 of the ultrasonic transducer array 200. The wire bonding 218 can use, for example, gold wires 220, to achieve sufficient electrical contact.

Figure 2D:
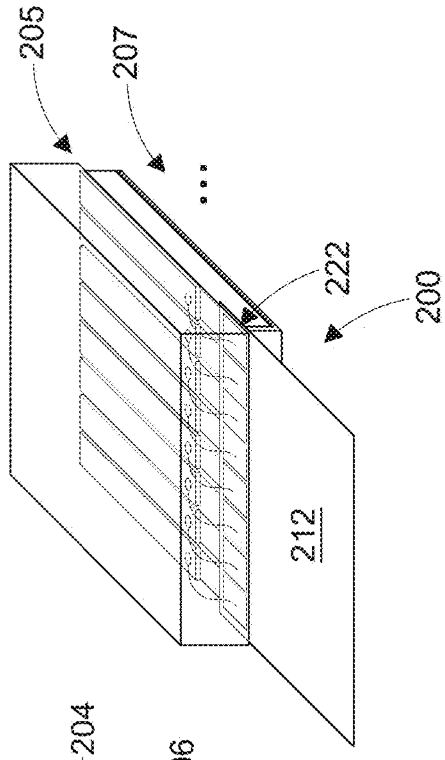

FIG. 2D shows an ultrathin backing layer 222 disposed over the back electrodes 204 wire bonded to FPCB 212. The backing layer 222 can be made, for example, from epoxy resin mixed with materials such as tungsten or alumina powder, forming the final assembly. The ultrathin backing layer 222 can correspond to the backing layer 102 of FIG. 1.

Implementations of the ultrathin ultrasound device (e.g., ultrathin ultrasound device 100 of FIG. 1 and ultrathin ultrasound device 200 of FIGS. 2A to 2D) described in the present disclosure can include several layers that synergistically enhance ultrasound imaging performance while maintaining a compact form suitable for wearable applications, as further explained below.

The implementations include a backing layer specifically adapted for the ultrathin ultrasound device, e.g., the backing layer 222. For example, the backing layer can be constructed as an ultrathin layer, e.g., approximately 0.5 to 3 mm in thickness. The exemplary backing layer can be composed of epoxy resin infused with high-density metal such as tungsten powder, silver powder, alumina powder, or carbon fiber. In some cases, the backing layer includes one or more metamaterials. The high acoustic impedance and attenuation properties of these materials can effectively absorb unwanted acoustic waves emanating from the back of the transducer elements, thereby significantly reducing, or minimizing, reflections and reverberations that could degrade image quality. The backing layer's composition and thickness can be optimized to achieve maximum acoustic absorption with minimal contribution to the overall device thickness, e.g., using one or more engineered materials. In some cases, the backing layer, such as the backing layer 222, can be composed, at least in part, of a metamaterial. Metamaterials can be used that can improve function of the backing layer 222, e.g., by at least one of maximizing acoustic absorption or minimizing contribution to overall device thickness.

The implementations include an ultrasonic transducer array with transducer elements made from piezoelectric materials, such as single crystals (e.g., PMN-PT), composites, or PZT ceramics. Single-crystal materials can offer superior electromechanical coupling coefficients and broader bandwidth compared to traditional ceramics, which can enhance image resolution and penetration depth. Each element within the ultrasonic transducer array can include front and back electrodes, which can allow for electrical excitation to generate ultrasound waves. The transducer elements can be arranged in linear, phased, curved, matrix arrays, and other customized morphologies depending on the desired imaging application.

The implementations include a special purpose FPCB with significantly reduced (or minimized) footprint. The special purpose FPCB can be connected to the ground electrodes of the transducer array through conductive epoxy bonding or soldering. The connection between the FPCB and the back electrodes of the transducer elements can be established using wire bonding, e.g., employing gold wires that can have a diameter of approximately 25 micrometers, for example. This arrangement can help reduce, or significantly reduce, the coverage area of the FPCB over the transducer, thereby decreasing the obstruction of the metal layer and enhancing the acoustic performance. The FPCB's design can include microvias and fine traces to accommodate high-density interconnections required for advanced transducer arrays.

The implementations can include one or more matching layers disposed between the transducer array and the acoustic lens. The one or more matching layers are characterized by a corresponding acoustic impedance that is between that of the transducer element and that of the acoustic lens. Each matching layer is a quarter wavelength in thickness. The configuration can achieve efficient transmission of ultrasonic waves from the transducer elements to the acoustic lens and ultimately into the tissue. Moreover, the matching layers can be designed with specific acoustic impedances to optimize impedance matching between the piezoelectric elements and the biological medium, thereby improving energy transmission efficiency and reducing signal loss. Materials such as epoxy resins filled with alumina or silica powders can be used, with thicknesses typically equal to one-quarter wavelength of the operating frequency, for example.

The implementations can include an acoustic lens. The acoustic lens can be the final layer that can focus the ultrasonic waves produced by the transducer array. The acoustic lens can be made from materials such as silicone rubber or polyurethane, so that the lens has a specific curvature designed to focus the ultrasound beam at a desired focal depth. This focusing capability can be vital for improving the resolution and sensitivity of the ultrasound image, particularly in applications requiring high precision.

The implementations can achieve an ultrathin design for wearable applications. The overall thickness of the device can preferably be kept under 5 mm, if not thinner, making the device ideal for integration into wearable technologies. By optimizing each layer's thickness and judiciously selecting materials that contribute to weight reduction without compromising performance, the device can deliver a compact, portable ultrasound device suitable for medical imaging in various clinical and remote health monitoring scenarios. The ultrathin design can also enhance patient comfort and allow for continuous monitoring without impeding mobility.

The implementations can leverage advanced fabrication techniques such as micro-electromechanical systems (MEMS) processing, precision dicing, and thin-film deposition to achieve the ultrathin form factor and high-density interconnections. These techniques can ensure high reliability and consistency across the transducer array, which can be critical for high-quality imaging.

The implementations can achieve integration with wearable electronics. For example, using the special purpose FPCB with a significantly reduced footprint, the implementations allow for seamless integration with wearable electronic modules, including signal processing units, power management circuits, and wireless communication interfaces. This integration can enable real-time data acquisition and transmission for remote diagnostics and telemedicine applications.

In some implementations, the ultrathin wearable ultrasonic transducer device can be manufactured consistent with illustrations provided in FIGS. 1 and 2A-2D and including specific steps as detailed below.

During transducer array fabrication, piezoelectric materials such as single crystals or PZT ceramics can be processed to form the transducer array. This can involve precision cutting (or dicing) to create individual transducer elements with specified dimensions, typically using a high-precision dicing saw or laser micromachining, for example.

During electrode formation, front and back electrodes can be deposited on each transducer element using thin-film deposition techniques, such as sputtering or evaporation. Materials such as gold or platinum can be used for their excellent electrical conductivity and biocompatibility.

During FPCB attachment, a special-purpose FPCB can be prepared with fine traces and microvias to match the transducer array's layout. The special-purpose FPCB can be attached to the front (ground) electrodes of the transducer elements using conductive epoxy bonding or soldering. The attachment can include precise alignment to achieve proper electrical connections.

During wire bonding, the back electrodes of the transducer elements can be connected to the FPCB using gold wire bonding. Ultrasonic or thermosonic bonding techniques, for instance, can be employed to create reliable interconnections. In some implementations, the wire bonds can have diameters of approximately 25 micrometers, for example, to minimize mass and potential acoustic interference.

When applying one or more matching layers over the transducer array, the matching layers can be formulated with materials that have specific acoustic impedances to optimize energy transmission. The layers can be applied using techniques such as molding or spin coating, for example, to achieve uniform thickness and surface quality.

When integrating an acoustic lens, the acoustic lens can be made, for example, from silicone rubber or polyurethane can be positioned over the matching layer(s). The lens can be molded directly onto the assembly or attached using a thin layer of acoustic coupling material.

When applying the backing layer to the rear of the transducer array, a mixture of epoxy resin and high-density materials (e.g., tungsten powder), for instance, can be prepared and applied using casting or molding techniques. The backing layer can be cured to achieve the desired mechanical and acoustic properties.

When encapsulating the final assembly, a biocompatible material can be used to protect the device from environmental factors and ensure patient safety. Examples of such materials include medical-grade silicone.

During testing and calibration, the electrical functionality and acoustic performance can be verified to confirm that the device meets the specifications for imaging resolution and sensitivity.

Figure 2E:
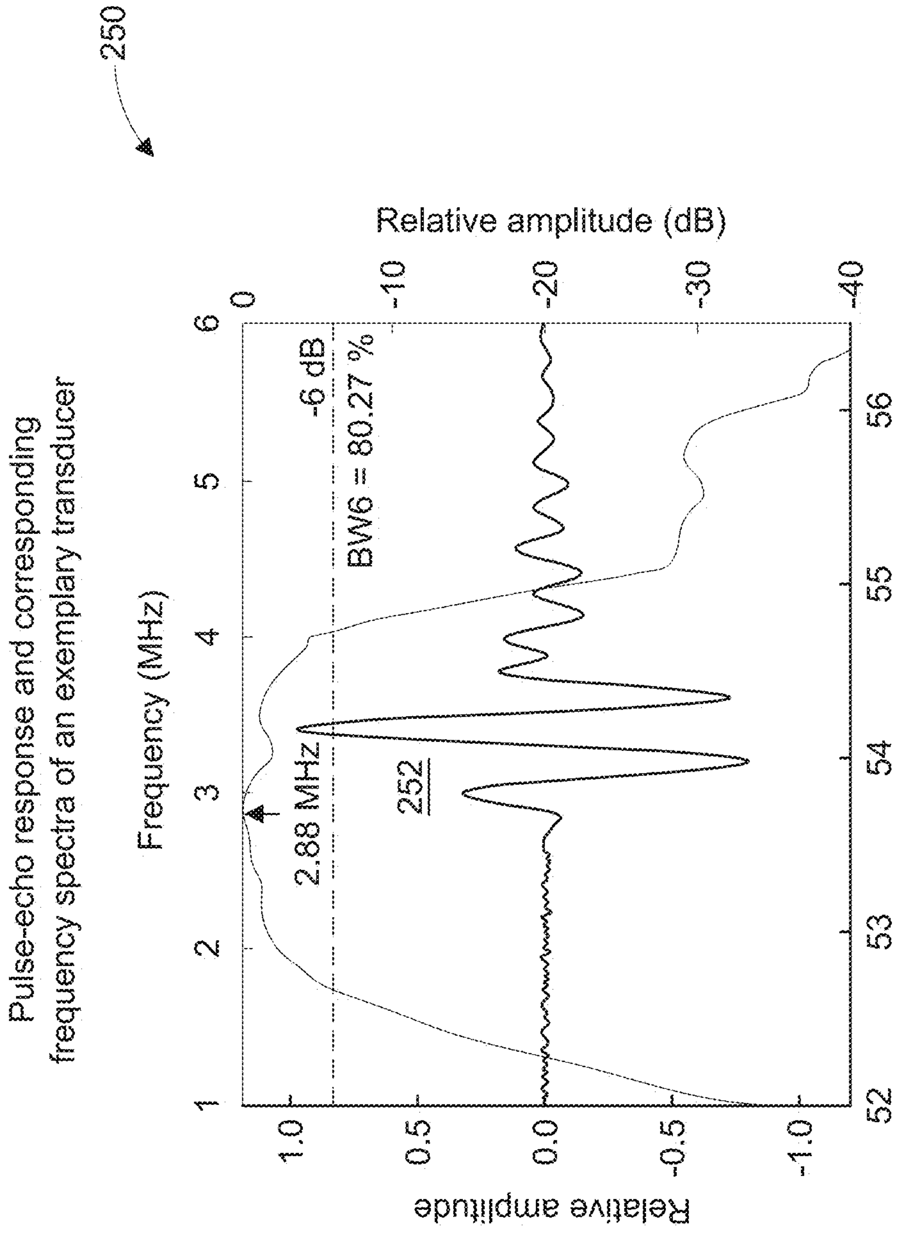
FIG. 2E shows an example of pulse echo measurements from testing an exemplary ultrathin ultrasound transducer.

FIG. 2E shows an example 250 of pulse-echo measurements from testing an exemplary ultrathin ultrasound transducer array, such as the ultrathin ultrasound device 100 of FIG. 1. The example 250 shows an instance of measured echo signal 252, which represents a reflection signal from, e.g., a reflecting surface. In some cases, an ultrathin ultrasound transducer array can include one or more elements, such as 64 elements. In the example 250, echo signal 252 exhibits an attenuating tail, representing reduced reverberation. The spectrum of echo signal 252 exhibits a center frequency of 2.88 MHz, and with a fractional bandwidth of 80.27%, which is often defined as the measured full-width-half-maximum (FWHM) over the measured center frequency. As shown in example 250, the FWHM (i.e., 6 dB width) is about 2.31 MHz. In some cases, a fractional bandwidth over 50% can be considered wide. In other cases, a fractional bandwidth over 70% can be considered as ultrawide. The broad bandwidth enables a wide range of applications such as harmonic imaging where the transducer can be configured to transmit probing pulses at a center frequency of, e.g., 2 MHz, and receive echo signals centered at, e.g., 4 MHz. These examples demonstrate greater image flexibility by transmitting pulses at a lower frequency to penetrate deeper tissues while resolving fine details carried by higher frequency echo signals. Indeed, the examples can facilitate a wide range of imaging applications for various organs (e.g., cardiac, abdominal, vascular, or musculoskeletal). In addition to harmonic imaging, the wide fractional bandwidth can also lend itself to frequency compounding where images from a series of frequency bins can be integrated or averaged to improve image quality (e.g., to reduce speckle appearance). In some cases, the average can be intensity based. In other cases, the average can be based on amplitude. Lastly, all things being equal, the wide fractional bandwidth can also allow for a superior axial resolution when compared to a narrower fractional bandwidth.

The ultrathin ultrasonic device can be integrated with wearable electronic modules, including signal processing units, power management circuits, and wireless communication interfaces. This integration can involve incorporating the device into a wearable form factor such as a patch or band.

Adjustable Patch for Securing Ultrasonic Transducers

The present disclosure further relates to an adjustable patch designed for securing an ultrasonic transducer to a body surface, allowing for extended, stable ultrasound monitoring from the body surface using the ultrathin ultrasonic device described above. The adjustable patch can include an adjustment base with an elastic clip that can be tightened or loosened using an adjustment knob to fix or release the transducer array onto the skin. An angle adjustment mechanism can allow precise alignment of the transducer for optimal imaging quality. A mounting plate integrated with a gel sprue can facilitate continuous replenishment of ultrasound gel, maintaining sufficiently effective coupling during long-term use. The mounting plate can be adaptable to different types of transducer arrays, e.g., linear, phased, curved, matrix arrays, and other customized morphologies, allowing for proper attachment for various imaging requirements. The patch size can also be adjustable to fit different anatomical locations and different aspect ratios of the ultrasonic transducer. For example, different ultrasonic transducer types and sizes can be used for monitoring different organs. Additionally, breathable medical tape can be used to secure the patch comfortably to the skin, reducing irritation during prolonged use. This adjustable patch system can provide reliable and consistent imaging, making it suitable for wearable and continuous ultrasound monitoring in clinical settings, including operating rooms, intensive care units, and remote patient monitoring.

Ultrasound imaging technology is widely applied in the fields of tissue imaging and pathological diagnosis. The devices used for ultrasound detection, referred to as ultrasonic probes, play a decisive role in determining the quality of the imaging results. In current clinical practice, most ultrasound probes are handheld and manually operated by medical practitioners. The physician places the probe on the patient's body and adjusts its position and angle to acquire the desired images. This process, while effective for intermittent imaging, presents significant challenges during long-term monitoring. Handheld ultrasound systems are labor-intensive, requiring constant manual operation, and even slight changes in the handholding position can lead to variability in image quality. Consequently, manual operation is often unsuitable for extended diagnostic sessions or for applications requiring consistent monitoring. The lack of a reliable, long-term monitoring capability often results in incomplete or degraded diagnostic information.

Moreover, in critical care settings such as intensive care units or during surgical procedures, continuous monitoring of physiological parameters is essential. The ability to perform continuous ultrasound monitoring can provide real-time information on organ function, blood flow, and other critical parameters. However, the absence of a stable, long-term attachment mechanism for ultrasonic transducers limits the use of ultrasound in these settings.

Implementations described in the present disclosure can address industry-side shortcomings by providing an adjustable patch system capable of securely fixing ultrasonic transducers of various shapes to the patient's body with precision and stability, allowing for adjustment of the transducer's angle and pressure. The techniques include features of an adjustment base for pressure control, an angle adjustment mechanism for optimizing the probe's orientation, and a mounting plate equipped with a gel sprue for continuous gel replenishment. These features can achieve sufficiently effective coupling over time and can significantly enhance the quality and reliability of ultrasound imaging, particularly for wearable or long-duration monitoring applications.

In summary, the implementations incorporate an adjustable patch for securing an ultrasonic transducer onto a patient's body for extended monitoring. For example, the adjustable patch can be used to house the ultrathin ultrasound device 100 described with reference to FIGS. 1 and 2A to 2B. The adjustable patch can include an adjustment base to secure the ultrasonic transducer in place. The adjustment base utilizes an elastic adjustment mechanism that can be tightened or loosened using an adjustment knob, enabling precise control of the transducer's positioning to the skin. The adjustable patch can include a mounting plate incorporating an ultrasound gel sprue (e.g., a channel for adding ultrasonic gel) that allows the ultrasound gel to be added during continuous monitoring. This arrangement can maintain coupling quality throughout the entire duration of monitoring, even in extended sessions such as several days to several weeks. The mounting plate is equipped with an angle adjustment feature, allowing users to change the orientation of the transducer relative to the body surface. The adjustability can facilitate targeting at specific imaging angles so that image quality can be improved. The implementations can accommodate adjustable mounting morphology to allow the patch to adapt to different types of ultrasonic transducer arrays, such as linear arrays, phased arrays, curved arrays, matrix arrays, and other customized morphologies. This feature enables the patch to accommodate and securely attach transducers of varying shapes and configurations, ensuring proper alignment and functionality for diverse clinical applications. The implementations can incorporate adjustable patch size to fit different body areas effectively. This feature allows for adaptability, making the patch versatile for use on patients of varying body sizes and for different target regions. The implementations incorporate breathable medical tape to enhance comfort and allow for extended use. The breathable nature of the tape prevents skin irritation and allows the patch to be comfortably worn for extended periods.

Figure 3A:
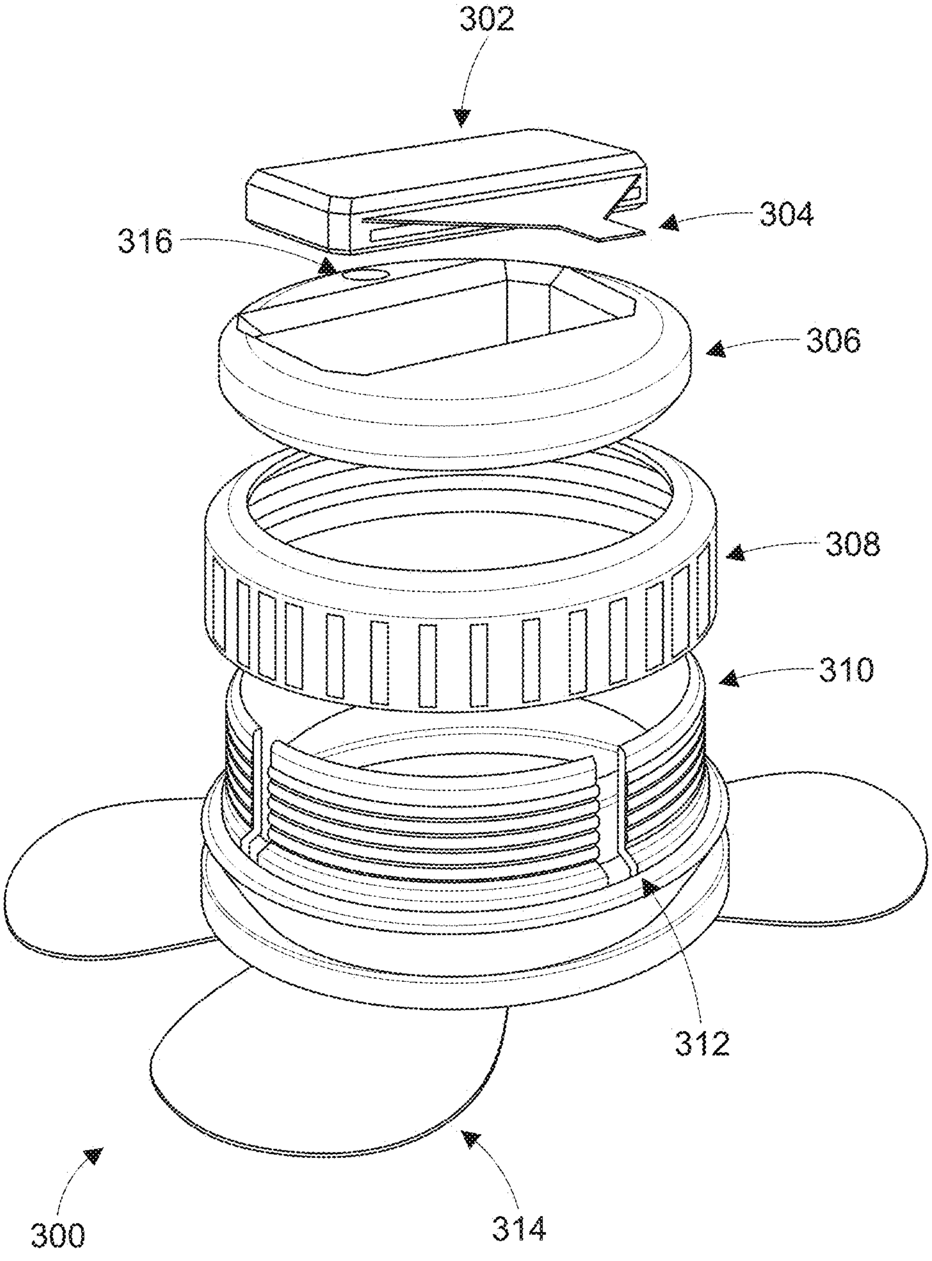
FIG. 3A is an exploded view of an adjustable patch according to some implementations of the present disclosure.

In more detail, FIG. 3A is an exploded view of an adjustable patch 300 for securing the ultrasonic transducer. As illustrated in FIG. 3A, components of the adjustable patch 300 can include an ultrasonic transducer array 302 (e.g., the ultrathin ultrasound device 100 described with reference to FIGS. 1 and 2A to 2B), an external connection 304, a mounting plate 306, an adjustment knob 308, an elastic clip 310, an adjustment base 312, and breathable medical tape 314.

A gel sprue 316 that is incorporated in the mounting plate 306 can make it possible to inject (e.g., by a syringe or squeeze bottle) or otherwise deliver ultrasound gel into the cavity between the ultrasonic transducer array 302 and the skin. The cavity in this case is further defined by the mounting plate 306, the adjustment knob 308, the elastic clip 310, the adjustment base 312, and the skin. The gel sprue serves as a hole (or orifice) for injecting replenishment gel.

In some implementations, the portion of the adjustable patch 300 that is initially attached to the skin includes all components except for the ultrasonic transducer array 302 (with the external connection 304) and mounting plate 306. Then, the mounting plate 306 containing the ultrasonic transducer array 302 can be pushed into the adjustment base 312. Adjustments can then be made to the adjustable patch 300 before ultrasound gel is added.

The adjustment knob 308 is operable by an operator to change the angle of the ultrasonic transducer relative to the surface of the skin. For example, the adjustment knob 308 can be adjusted relative to the adjustment base 312 that dwells on the skin of the subject. The adjustment can be made, for example, by rotating the adjustment knob 308 along threads on the adjustment knob 308 that match mated threads on the adjustment base 312. In some implementations, the mated threads can be implemented by the elastic clip 310, which can be a notched, spring-loaded mechanism that allows the adjustment knob 308 to secure the ultrasonic transducer array 302 with the mounting plate 306 at a preferred angle relative to the skin. In some implementations, the ultrasonic transducer array 302 can be adjusted relative to the mounting plate, such as by rotating or tilting on pins at two ends of the ultrasonic transducer array 302 that are mounted in the mounting plate 306. The adjustable base 312 is open, so that nothing in the adjustable patch 300 obstructs signals received by the ultrasonic transducer array 302.

The external connection 304 can be connected (e.g., using a cable or flexible printed circuits (FPC)) to a control system, such as the pocket size control system described with reference to FIGS. 5A and 5B. The breathable medical tape 314 can be fastened directly to smooth skin or to partially hairy skin, or to hair for which gaps in the hair have been filled in with a material that provides a suitable base for adhesion by the breathable medical tape 314. The external connection 304 can include a flat cable connected to the ultrasonic transducer array 302, e.g., in the middle of the ultrasonic transducer array 302.

Figure 3D:
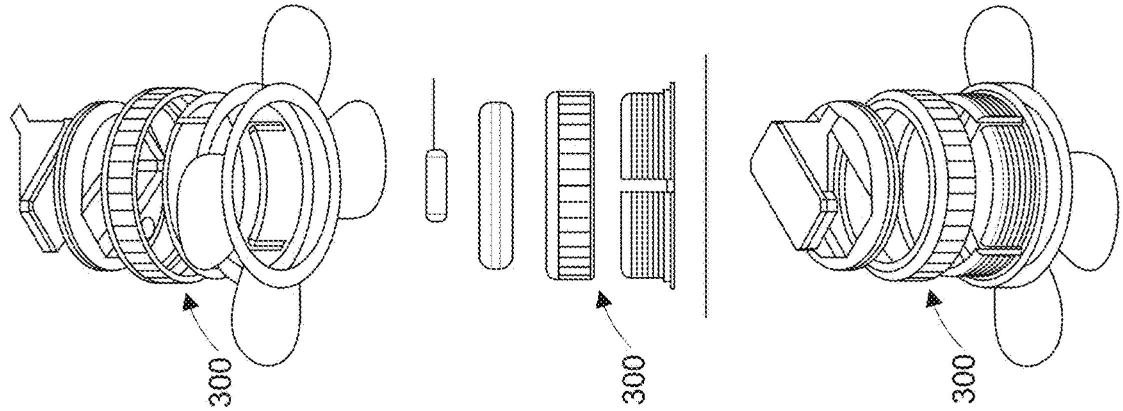
FIGS. 3B to 3D respectively show various perspective views and side views of the adjustable patch of FIG. 3A as assembled.
Figure 3C:
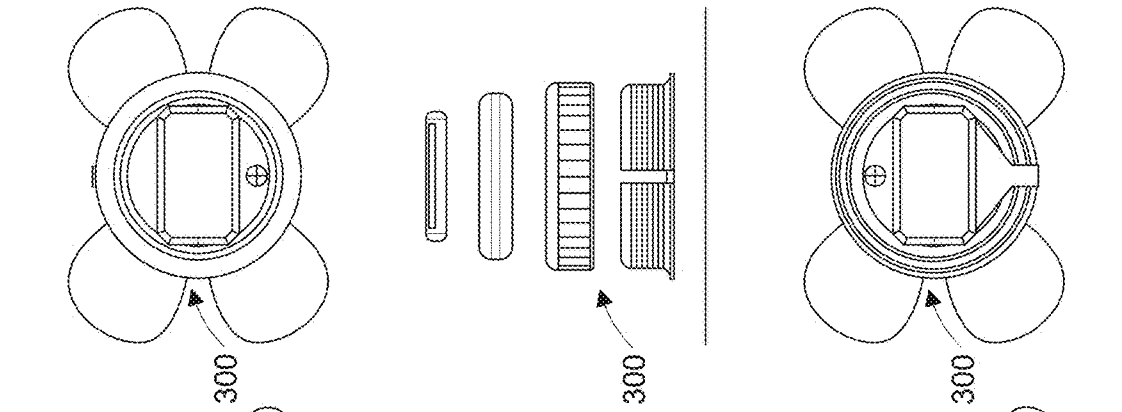
Figure 3B:
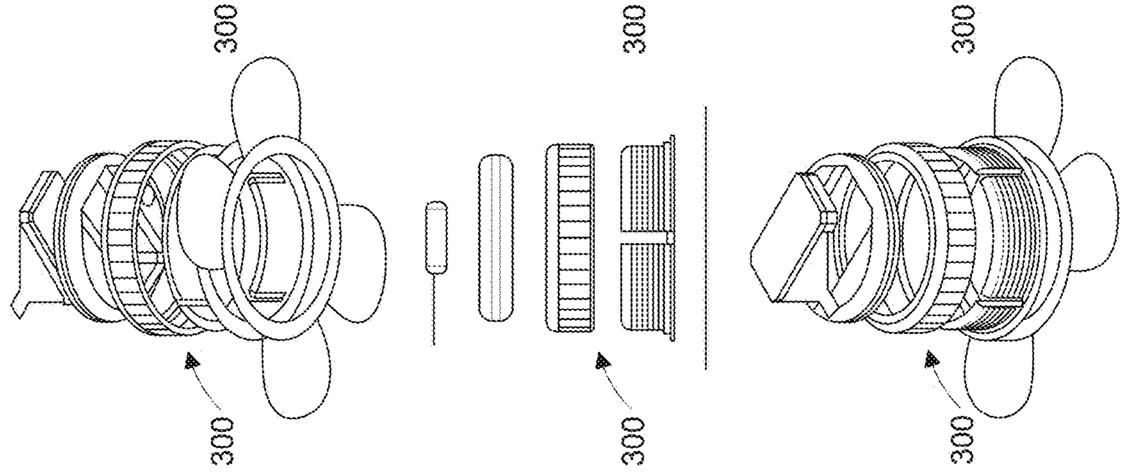

FIGS. 3B-3D show different view angles of the adjustable patch 300 of FIG. 3A, highlighting the patch's various components and how the components interact. Specifically, the upper panel of FIG. 3B shows the lower right view, while the middle panel and the lower panel respectively show the right view, and upper right view of the adjustable patch. In FIG. 3C, the upper panel, the middle panel, and the bottom panel respectively show the bottom view, the front view, and the top view of the adjustable patch 300. FIG. 3D shows the lower left view, the left view, and the upper left view of the adjustable patch 300 respectively in the top, middle and lower panels. FIGS. 3B to 3D thus include multiple perspective views to better illustrate the overall structure and design features of the patch.

Figure 4A:
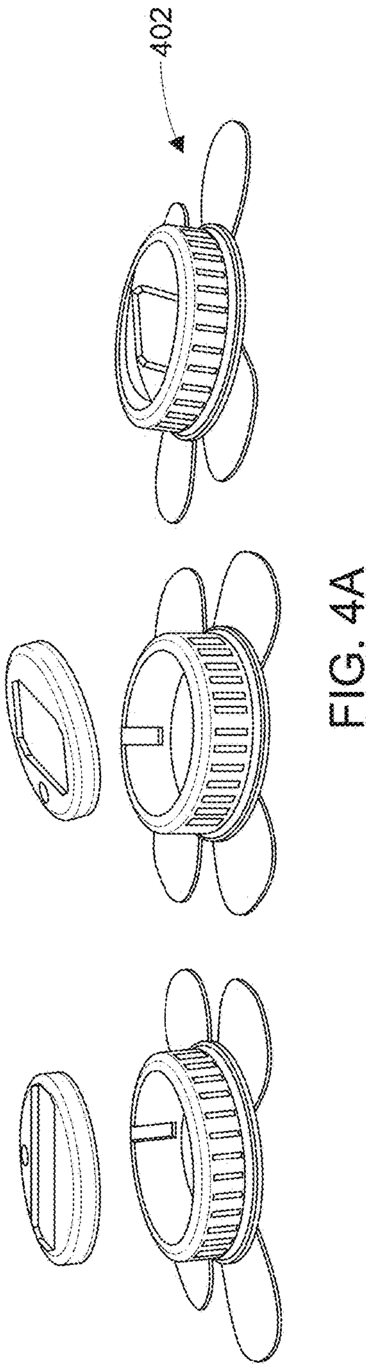
FIGS. 4A to 4C illustrate various adjustable aspects of the adjustable patch of FIG. 3A.

FIG. 4A is a diagram demonstrating an adjustable plate angle mechanism 402 of an adjustable patch and its impact on transducer alignment. For example, the adjustable patch 400 can be the adjustable patch 300. By virtue of the adjustable plate angle, the orientation of the ultrasonic transducer array 302 with respect to the skin position of the subject can be adjusted to facilitate optimal viewing.

Figure 4B:
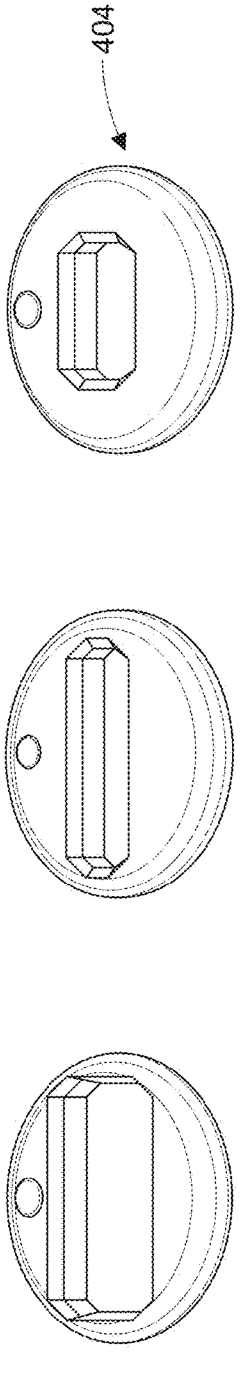

FIG. 4B is a diagram illustrating an adjustable mounting morphology of an adjustable patch, showing how the patch can adapt to accommodate different ultrasonic transducer arrays (e.g., linear, phased, curved, matrix arrays, and other customized morphologies). Examples can include the interchangeable adapter modules or adjustable clamps that can be used for different transducer types.

Figure 4C:
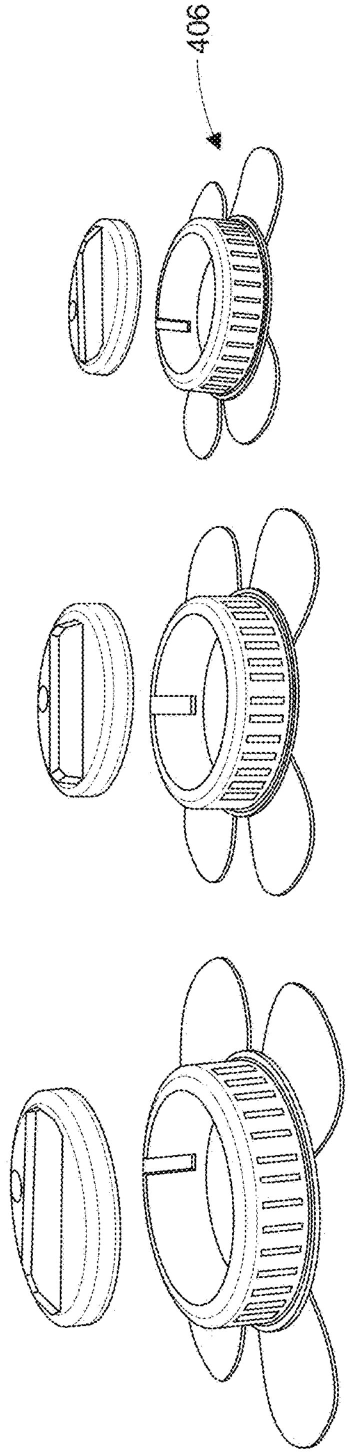

FIG. 4C is a diagram illustrating an adjustable patch size, demonstrating how the patch can be resized to fit different body areas and accommodate subjects of varying body sizes. Examples can include the interchangeable adapter modules.

The adjustable patch for securing ultrasonic transducers described herein can be designed to overcome the limitations of existing handheld ultrasound probes. The present disclosure describes several innovative components, each intended to facilitate extended use and to improve the stability, quality, and comfort of ultrasound monitoring.

The adjustment base 312 can include the elastic clip 310 coupled with the adjustment knob 308 that can serve to securely fix or release the ultrasonic transducer array to the patient's skin. By rotating the adjustment knob 308, the user can either tighten or loosen the elastic clip 310, allowing the transducer array to be easily attached or detached. This feature can ensure a stable connection between the transducer and the skin, which can be crucial for consistent imaging results during monitoring sessions.

The mounting plate 306 can hold the transducer firmly in place and can include an integrated gel sprue. The gel sprue can facilitate the continuous addition of ultrasound gel, which may be critical during prolonged monitoring sessions where the gel tends to dry out over time. By enabling the gel to be replenished without detaching the transducer, the designs described in the present disclosure can ensure consistent and high-quality acoustic coupling, thereby maintaining the integrity of the ultrasonic waves.

The adjustable plate angle feature 402 can allow the user to change the orientation of the ultrasonic transducer relative to the skin surface. This capability can be particularly important for applications in which specific imaging angles may be required to obtain the best possible image quality. The ability to adjust the angle without detaching or repositioning the patch can ensure a continuous and uninterrupted monitoring process.

The adjustable mounting morphology 404 can allow the patch to adapt to different types of ultrasonic transducer arrays, including linear arrays, phased arrays, curved arrays, matrix arrays, and other customized morphologies, each of which has its own specific configuration and requirements. The mounting plate 306 can include interchangeable adapter modules or adjustable clamps that can be reconfigured or swapped out to match the specific transducer design. These adapters ensure that the transducer is held securely and aligned correctly, optimizing the acoustic performance and image quality. The system may include a set of standardized adapters compatible with common transducer models or custom adapters for specialized applications.

The adjustable patch size mechanism 406 can allow the patch to be resized to accommodate different body parts or patient sizes. This flexibility can ensure that the patch can be used for a wide range of applications, from neonatal care to adult monitoring, providing a secure fit irrespective of the application site.

The breathable medical tape 314 can be used to attach the patch securely to the patient's skin while allowing for air circulation. The tape can be made from hypoallergenic, non-irritating materials such as non-woven fabrics with microporous structures that permit moisture vapor transmission. The tape can include an adhesive layer with gentle, skin-friendly adhesives that provide secure attachment without causing skin damage upon removal. Additionally, the tape can have antimicrobial properties to reduce the risk of infection during prolonged use.

Wearable Ultrasound System

Some implementations include a wearable ultrasound system incorporating, for example, a portable control system, an ultrasound cable or flexible printed circuit (FPC), an ultrasonic transducer array, and an adjustable patch. In the wearable ultrasound system, the portable control system can connect to the ultrasonic transducer array via one or more ultrasound cables or FPCs, while the transducer array is secured to the body of the subject using the adjustable patch for monitoring the subject. The portable control system can communicate wirelessly with one or more external smart devices, such as smartphones, tablets, or computers, for example, using a wireless communication protocol. This enables real-time ultrasound imaging display and control of system parameters on the external devices. The wearable ultrasound system is suitable for continuous monitoring applications in various clinical settings, thereby providing improved mobility and real-time access to medical imaging without the need for bulky monitoring equipment. The implementations of the disclosure can overcome shortcomings of existing ultrasound systems by offering a compact, comfortable, and easily adjustable solution for both diagnostic imaging at point-of-care and long-term monitoring at home or a long-term care facility.

For context, traditional ultrasound systems are associated with relatively large size and more restricted usage conditions, which can lead to generally complicated maintenance infrastructure and manual operation by medical professionals. These traditional systems typically include a bulky ultrasound scanner (e.g., a cart-based system) connected to an ultrasound transducer manually applied by a practitioner on the patient's body to scan the patient during short, intermittent examinations. While such systems may be effective for real-time imaging during sonographic examinations, these systems are not well-suited for prolonged monitoring as implicated by the size of the traditional ultrasound system and the associated need for continuous operator involvement.

More modern systems incorporate portable ultrasound devices to result in significantly reduced size when compared to earlier models, making them more convenient for use in a wider range of environments. Despite the improved portability, such portable ultrasound scanners still involve constant manual operation, and as such, can provide only intermittent assessments rather than continuous and consistent monitoring. Because of the inability to maintain stable, long-term contact between the wave-emitting ultrasonic transducer and the body, these portable ultrasound scanners have limited use in applications that demand constant supervision, such as intensive care or emergency scenarios.

Implementations of the present disclosure can address these issues by providing a wearable ultrasound system that incorporates an adjustable patch to securely attach the wave-emitting ultrasonic transducer array to the patient's body while a controller unit interacts with the ultrasonic transducer array to insonify a bodily region, acquire pulse-echo signals from the insonified bodily region, perform beamforming to generate an ultrasound image of the bodily region. This design can maintain stable contact without the need for continuous manual application, thus enabling long-term monitoring. Additionally, the control unit is portable and can interact with the ultrasonic transducer array through a cable, FPC, or wirelessly. The portable control unit can further communicate wirelessly with external smart devices such as a smart phone device, or a flat panel display device, which allows for real-time visualization of ultrasound images, while maintaining control over the parameters of the ultrasonic transducer array so that adaptability and precision can be achieved during continuous monitoring.

Implementations of a wearable ultrasound system can feature a portable control system, an ultrathin ultrasonic transducer array, an adjustable patch, and wireless communication capabilities. This wearable ultrasound system is user-friendly, easy to operate, and capable of providing continuous monitoring based on real-time streams of ultrasound data acquired in-situ from the patient where healthcare professionals can respond quickly to changes in patient conditions. As described above, the ultrathin ultrasonic transducer array can be implemented as a patch sensor with a total thickness of less than 5 mm, capable of being affixed comfortably to various parts of the body with close contact for localized monitoring using reliable imaging. The ultrathin ultrasonic transducer array, as a patch sensor, can be mounted on the adjustable patch to accommodate various patient conditions for versatile positioning of the wave-emitting ultrasonic transducer array. The portable control system can be compact, lightweight, and wearable by the patient. As explained in more detail below, the portable control system provides computational capability for ultrasound imaging and wireless communication capabilities for interfacing with, for example, external devices.

Figure 5A:
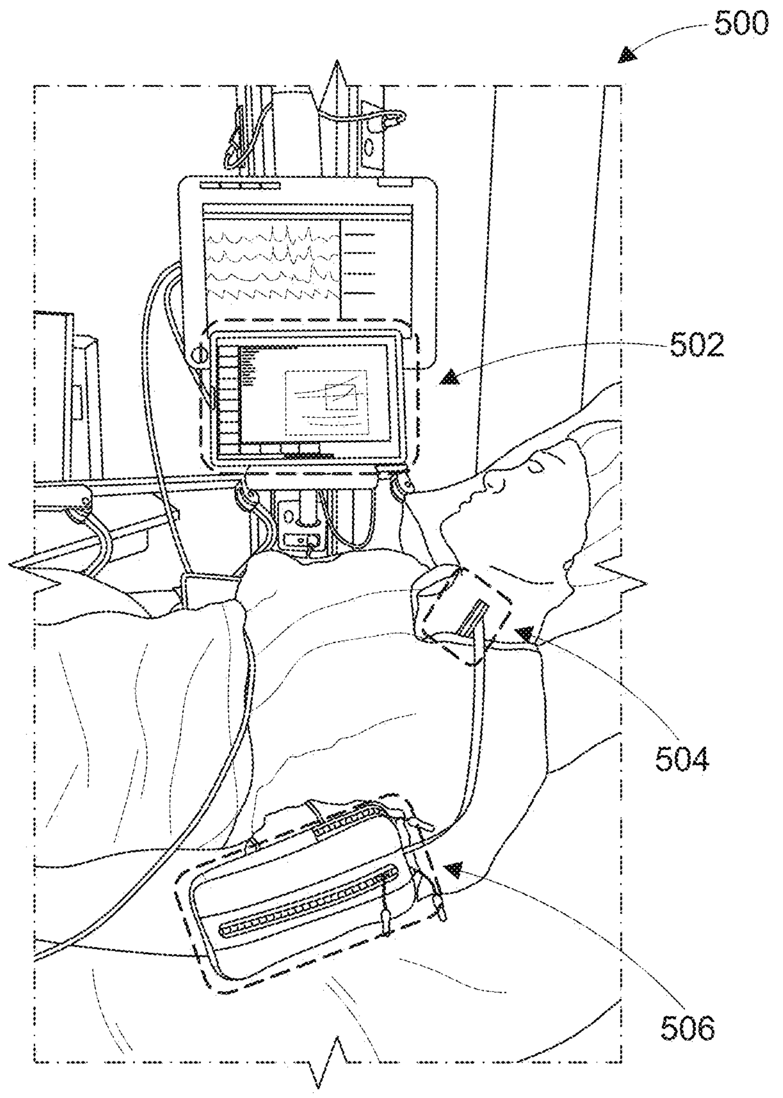
FIGS. 5A to 5C illustrate examples of using a wearable ultrasound system according to some implementations of the present disclosure.
Figure 5B:
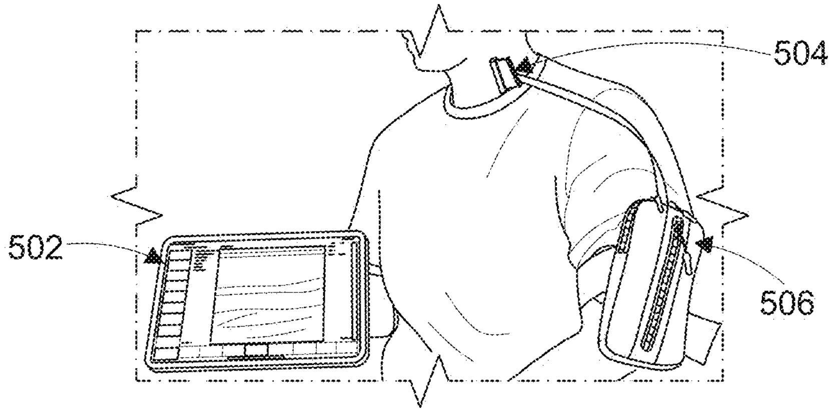
Figure 5C:
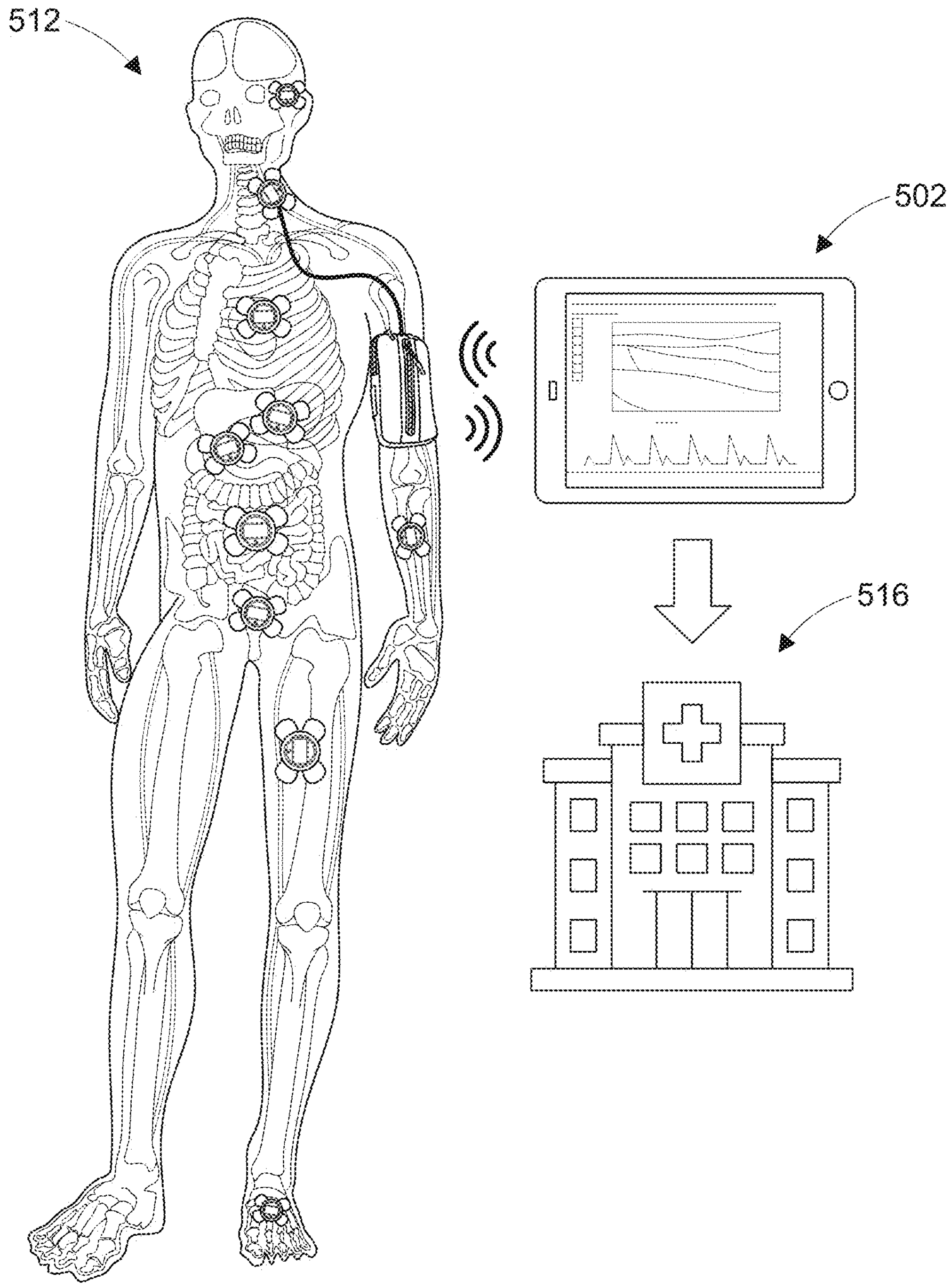

Referring to FIGS. 5A to 5C, the wearable ultrasound system 500 includes a portable control system 506, a wearable ultrasound patch 504 where an ultrathin ultrasonic transducer array is mounted inside an adjustable patch, and an external device 502. In an example use case scenario, the wearable ultrasound patch 504 is positioned on the skin of a subject's neck region to monitor the subject's left carotid artery. The wearable ultrasound patch 504 is securely attached to the neck skin using, for example, breathable medical tapes. The ultrathin ultrasonic transducer array, mounted inside the adjustable patch, emits ultrasound waves into the neck region and receive responsive echoes from the neck region. The wearable ultrasound patch 504 is connected via a cable or FPC to the portable control system 506, which provides the ultrathin ultrasonic transducer array with electrical pulses to generate the ultrasound waves for emission. As responsive echoes arrive at the ultrathin ultrasonic transducer array, electrical signals are generated by the ultrathin ultrasonic transducer array and then provided to the portable control system 506 by the cable or FPC. Thereafter, the portable control system 506 performs beamforming based on the acquired electrical signals and generates a beamformed ultrasound image of the neck region. During a monitoring operation, electrical signals are continuously acquired from the ultrathin ultrasonic transducer array, which can be positioned in a variety of positions on subject 512, for example, the cranial region, the neck region, the thoracic region, the abdominal regions, the bladder region, the leg region, the foot region, as well as the upper and lower arm regions, as depicted in FIG. 5C. In some cases, the beamformed ultrasound images are streamed to a flat panel display as an example of external device 502. Based on the results of the monitoring session, alerts can be generated and sent to a medical facility 516, such as a hospital.

As described above with references to FIGS. 1 and 2A to 2D, the ultrathin ultrasonic transducer array may have a typical thickness less than 5 mm, making the device lightweight and highly portable for wearable applications. The ultrathin ultrasonic transducer array can be constructed to include: a backing layer using, for example, an epoxy resin mixed with high-density metal or ceramic-based materials, such as tungsten powder, silver powder, alumina powder, or carbon fiber. The backing layer effectively absorbs unwanted acoustic waves while maintaining a minimal thickness. The ultrathin ultrasonic transducer array can be constructed to further include advanced materials such as single crystals, composite materials, or lead zirconate titanate (PZT) ceramics that offer high electromechanical coupling coefficients and broad bandwidth, enhancing the quality of imaging. The ultrathin ultrasonic transducer array can also be constructed using micromachined technologies involving capacitive micromachined ultrasonic transducer (CMUT) or piezoelectric micromachined ultrasonic transducer (PMUT). The ultrathin ultrasonic transducer array can be constructed to further include flexible printed circuit board (FPCB) connected to the ultrathin ultrasonic transducer array using conductive epoxy bonding or soldering, and wire-bonded with gold wires, which can reduce the FPCB's physical footprint over the transducer array, thereby reducing acoustic obstruction. The ultrathin ultrasonic transducer array can be constructed to additionally include acoustic lens made of silicone rubber or other suitable materials to focus the ultrasound waves being emitted to enhance imaging resolution and depth of field. The ultrathin ultrasonic transducer array can be constructed to further include one or more matching layers to improve transmission efficiency of the emitted acoustic waves by implementing impedance matching between the transducer array and the acoustic lens. Implementations of the present disclosure can reduce noise, enhance ultrasound imaging quality, and facilitate integration of the resulting system into a variety of medical and industrial applications where compact ultrasound solutions would be advantageous.

As described above with references to FIGS. 3A to 3D and 4A-4C, the adjustable patch can secure the ultrathin ultrasonic transducer array to the patient's body for extended monitoring. The adjustable patch can include an adjustment base and a mounting plate with gel spruce. The adjustment base can incorporate an elastic mechanism capable of being tightened or loosened via an adjustment knob to achieve precise control over the transducer's positioning relative to the subject's body. The mounting plate allows for continuous addition of ultrasound gel to maintain sufficient coupling quality for extended monitoring periods, ranging from several hours to days. The plate angle can be adjusted, allowing for fine tuning of the orientation of the emitting surface of the ultrathin ultrasonic transducer array relative to the body surface to improve targeting using specific imaging angles. The patch can adapt to a variety of ultrasonic transducer array configurations, including linear, phased, curved, matrix arrays, and other customized morphologies so that a diverse set of clinical applications can be pursued. The size of the patch can be modified to accommodate different body areas, rendering the resulting system versatile for patients of varying body sizes and for different target regions. The patch can use breathable medical tape to be securely affixed to the skin, reducing likelihood of irritation and allowing for extended comfortable use.

Figure 6A:
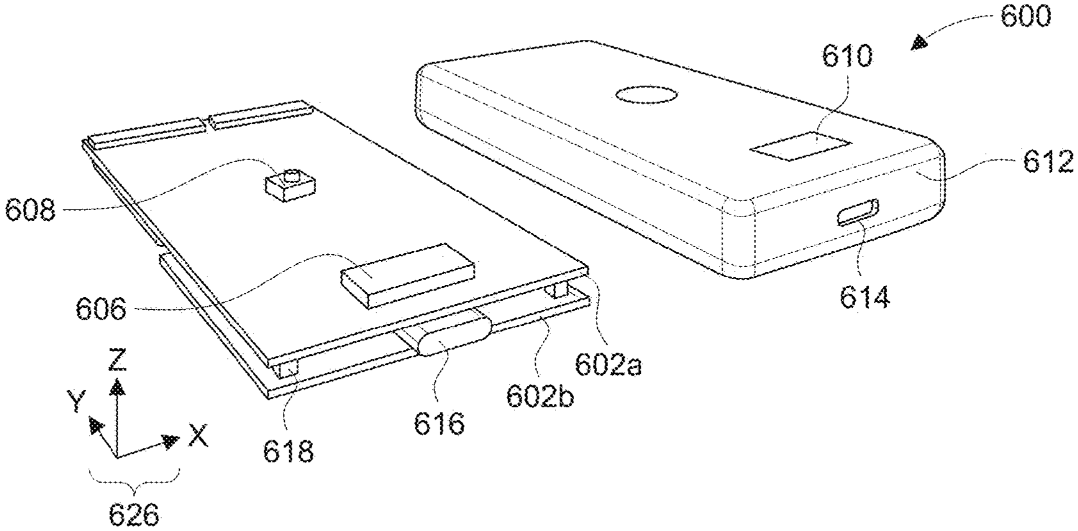
FIGS. 6A to 6B depict various components of a control system of the wearable ultrasound system illustrated in FIGS. 5A-5C.
Figure 6B:
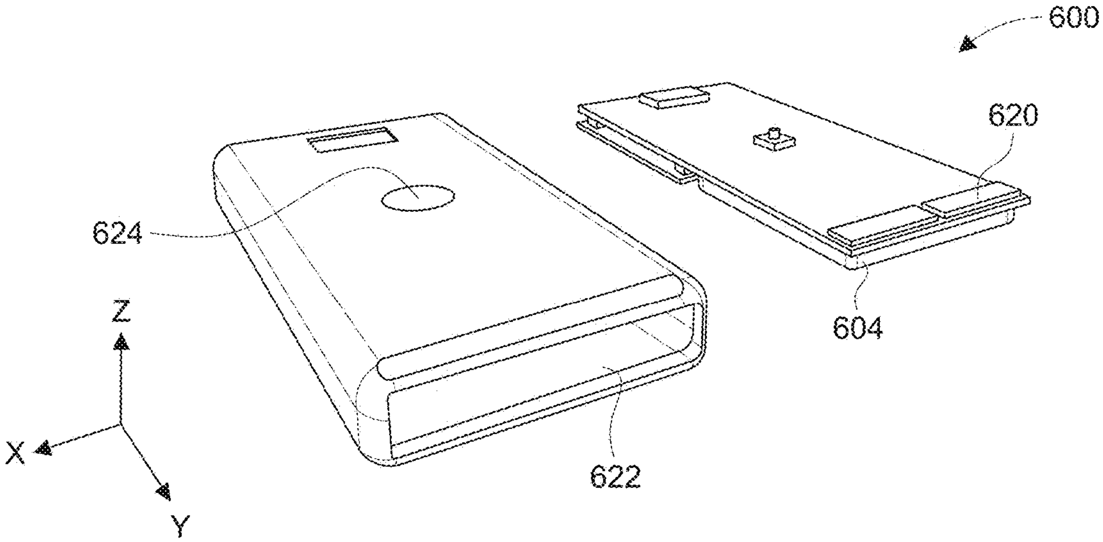

Further referring to FIGS. 6A-6B, the portable control system 506 can be implemented as a portable control system 600 housed in a compact casing (e.g., circuit housing 612) to enclose, for example, a primary circuit board 602*a*, a second circuit board 602*b*, and a battery module 604. The portable control system 600 can communicate with external devices (e.g., external device 502) using an integrated wireless module. The wireless communication capabilities allow for remote monitoring so that medical staff at medical facility 516 can monitor ultrasound images remotely on a tablet, mobile phone or computer, enhancing patient care in both clinical and home settings. The wireless communication capabilities also allow for adjustment of ultrasound acquisition parameters of the ultrathin ultrasonic transducer array from the remote devices operated by the medical staff. The portable control system 600 can have a user interface including control button 608 (e.g., power on/off and other manual operations), battery level display 606 with screen protector 610 (providing, e.g., visual indication of the device's power status), universal serial bus (USB) port 614 (e.g., driving USB module 616 on secondary circuit board 602*b*).

In more detail, the primary circuit board 602*a* can include circuit implementations such as field programmable gated array (FPGA), graphic processing unit (GPU), or application specific integrated circuit (ASIC) to handle ultrasound signal processing, image transmission and device control. For example, the circuit implementations can include one or more beamforming circuit to adaptively control the focal depth of each transmission event of the ultrathin ultrasonic transducer array that insonifies a region inside the subject, and dynamically generate the receive beams based on echo signals in response to each transmission event. The circuit implementations can include codec modules to transmit ultrasound images generated based on the beamformed signals to external device 502.

The secondary circuit board 604*b* can contain a power management module, a wireless communication module (e.g., WiFi/Bluetooth), and interfaces for wired connections (e.g., USB, firewire). For example, the power management module can manage battery charging, voltage regulation, and power distribution between various components such as the ultrathin ultrasonic transducer array, the primary circuit board, and the secondary circuit board. In one case, the power management module can manage power negotiation between devices so that the power supplied by the rechargeable battery can be advantageously provided to the ultrathin ultrasonic transducer array, the primary circuit board, and the secondary circuit board, enabling faster charging and more efficient energy use. In another, the power management module can regulate the voltage supplied to, for example, the ultrathin ultrasonic transducer array.

The battery module 604 can include a rechargeable battery (e.g., lithium-ion based) installed alongside the primary and secondary circuit boards to maintain compactness. The rechargeable battery can sustain long-duration operation of the portable control system 506 and the ultrathin ultrasonic transducer array. The battery module 604 can include a cable connector 620 for receiving a charging cable coupled to a power source (e.g., a power converter). In some cases, the battery module 604 can accommodate wireless charging.

Figure 7:
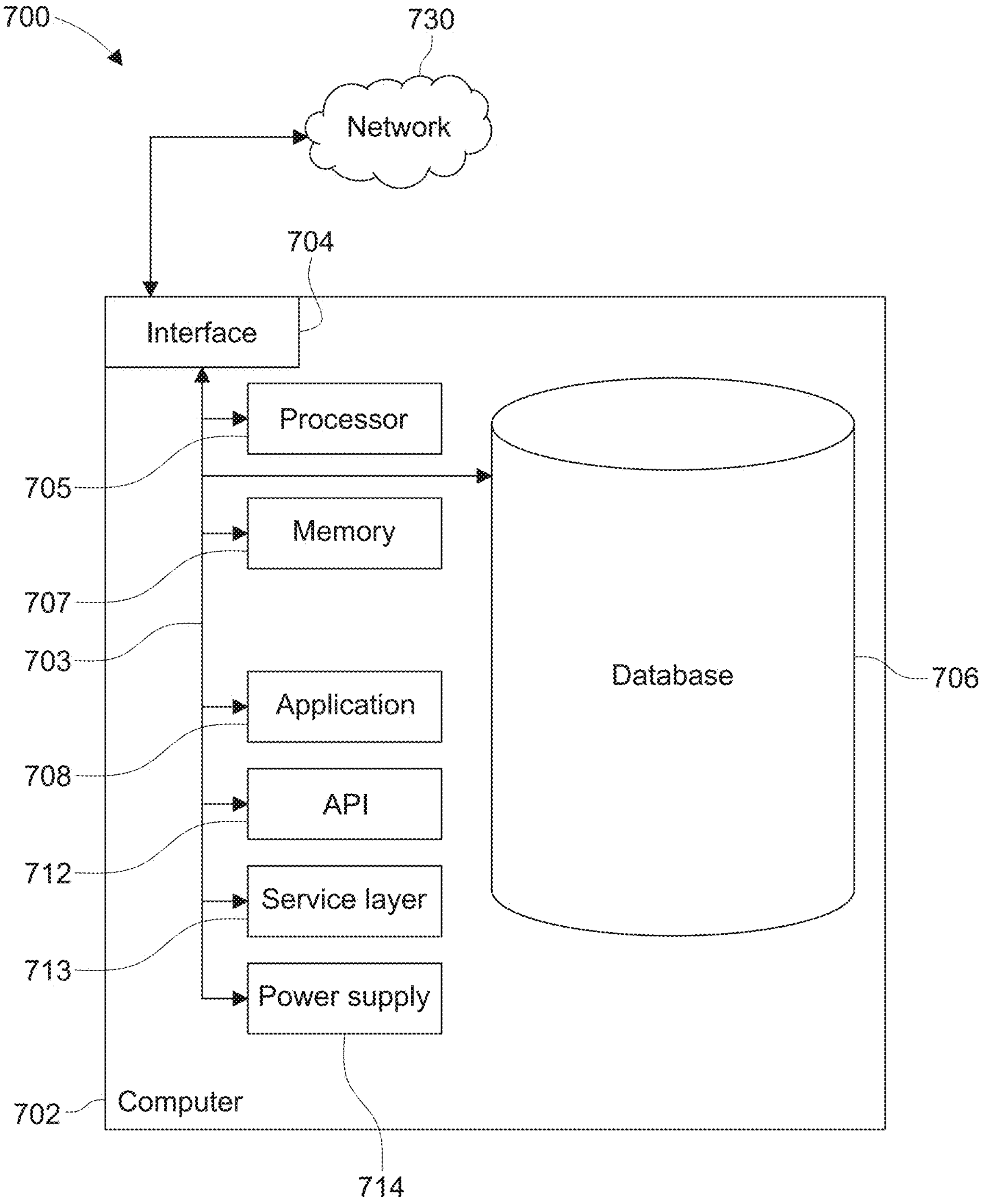
FIG. 7 is a block diagram illustrating an example computer system used to provide computational functionalities associated with described algorithms, methods, functions, processes, flows, and procedures as described in the present disclosure, according to some implementations of the present disclosure.

FIG. 7 is a block diagram of an example computer system 700 used to provide computational functionalities associated with described algorithms, methods, functions, processes, flows, and procedures described in the present disclosure, according to some implementations of the present disclosure. The illustrated computer 702 is intended to encompass any computing device such as a server, a desktop computer, a laptop/notebook computer, a wireless data port, a smart phone, a personal data assistant (PDA), a tablet computing device, or one or more processors within these devices, including physical instances, virtual instances, or both. The computer 702 can include input devices such as keypads, keyboards, and touch screens that can accept user information. Also, the computer 702 can include output devices that can convey information associated with the operation of the computer 702. The information can include digital data, visual data, audio information, or a combination of information. The information can be presented in a graphical user interface (UI) (or GUI).

The computer 702 can serve in a role as a client, a network component, a server, a database, a persistency, or components of a computer system for performing the subject matter described in the present disclosure. The illustrated computer 702 is communicably coupled with a network 730. In some implementations, one or more components of the computer 702 can be configured to operate within different environments, including cloud-computing-based environments, local environments, global environments, and combinations of environments.

At a top level, the computer 702 is an electronic computing device operable to receive, transmit, process, store, and manage data and information associated with the described subject matter. According to some implementations, the computer 702 can also include, or be communicably coupled with, an application server, an email server, a web server, a caching server, a streaming data server, or a combination of servers.

The computer 702 can receive requests over network 730 from a client application (for example, executing on another computer 702). The computer 702 can respond to the received requests by processing the received requests using software applications. Requests can also be sent to the computer 702 from internal users (for example, from a command console), external (or third) parties, automated applications, entities, individuals, systems, and computers.

Each of the components of the computer 702 can communicate using a system bus 703. In some implementations, any or all of the components of the computer 702, including hardware or software components, can interface with each other or the interface 704 (or a combination of both) over the system bus 703. Interfaces can use an application programming interface (API) 712, a service layer 713, or a combination of the API 712 and service layer 713. The API 712 can include specifications for routines, data structures, and object classes. The API 712 can be either computer-language independent or dependent. The API 712 can refer to a complete interface, a single function, or a set of APIs.

The service layer 713 can provide software services to the computer 702 and other components (whether illustrated or not) that are communicably coupled to the computer 702. The functionality of the computer 702 can be accessible for all service consumers using this service layer. Software services, such as those provided by the service layer 713, can provide reusable, defined functionalities through a defined interface. For example, the interface can be software written in JAVA, C++, or a language providing data in extensible markup language (XML) format. While illustrated as an integrated component of the computer 702, in alternative implementations, the API 712 or the service layer 713 can be stand-alone components in relation to other components of the computer 702 and other components communicably coupled to the computer 702. Moreover, any or all parts of the API 712 or the service layer 713 can be implemented as child or sub-modules of another software module, enterprise application, or hardware module without departing from the scope of the present disclosure.

The computer 702 includes an interface 704. Although illustrated as a single interface 704 in FIG. 7, two or more interfaces 704 can be used according to particular needs, desires, or particular implementations of the computer 702 and the described functionality. The interface 704 can be used by the computer 702 for communicating with other systems that are connected to the network 730 (whether illustrated or not) in a distributed environment. Generally, the interface 704 can include, or be implemented using, logic encoded in software or hardware (or a combination of software and hardware) operable to communicate with the network 730. More specifically, the interface 704 can include software supporting one or more communication protocols associated with communications. As such, the network 730 or the interface's hardware can be operable to communicate physical signals within and outside of the illustrated computer 702.

The computer 702 includes a processor 705. Although illustrated as a single processor 705 in FIG. 7, two or more processors 705 can be used according to particular needs, desires, or particular implementations of the computer 702 and the described functionality. Generally, the processor 705 can execute instructions and can manipulate data to perform the operations of the computer 702, including operations using algorithms, methods, functions, processes, flows, and procedures as described in the present disclosure.

The computer 702 also includes a database 706 that can hold data for the computer 702 and other components connected to the network 730 (whether illustrated or not). For example, database 706 can be an in-memory, conventional, or a database storing data consistent with the present disclosure. In some implementations, database 706 can be a combination of two or more different database types (for example, hybrid in-memory and conventional databases) according to particular needs, desires, or particular implementations of the computer 702 and the described functionality. Although illustrated as a single database 706 in FIG. 7, two or more databases (of the same, different, or combination of types) can be used according to particular needs, desires, or particular implementations of the computer 702 and the described functionality. While database 706 is illustrated as an internal component of the computer 702, in alternative implementations, database 706 can be external to the computer 702.

The computer 702 also includes a memory 707 that can hold data for the computer 702 or a combination of components connected to the network 730 (whether illustrated or not). Memory 707 can store any data consistent with the present disclosure. In some implementations, memory 707 can be a combination of two or more different types of memory (for example, a combination of semiconductor and magnetic storage) according to particular needs, desires, or particular implementations of the computer 702 and the described functionality. Although illustrated as a single memory 707 in FIG. 7, two or more memories 707 (of the same, different, or combination of types) can be used according to particular needs, desires, or particular implementations of the computer 702 and the described functionality. While memory 707 is illustrated as an internal component of the computer 702, in alternative implementations, memory 707 can be external to the computer 702.

The application 708 can be an algorithmic software engine providing functionality according to particular needs, desires, or particular implementations of the computer 702 and the described functionality. For example, application 708 can serve as one or more components, modules, or applications. Further, although illustrated as a single application 708, the application 708 can be implemented as multiple applications 708 on the computer 702. In addition, although illustrated as internal to the computer 702, in alternative implementations, the application 708 can be external to the computer 702.

The computer 702 can also include a power supply 714. The power supply 714 can include a rechargeable or non-rechargeable battery that can be configured to be either user- or non-user-replaceable. In some implementations, the power supply 714 can include power-conversion and management circuits, including recharging, standby, and power management functionalities. In some implementations, the power supply 714 can include a power plug to allow the computer 702 to be plugged into a wall socket or a power source to, for example, power the computer 702 or recharge a rechargeable battery.

There can be any number of computers 702 associated with, or external to, a computer system containing computer 702, with each computer 702 communicating over network 730. Further, the terms "client," "user," and other appropriate terminology can be used interchangeably, as appropriate, without departing from the scope of the present disclosure. Moreover, the present disclosure contemplates that many users can use one computer 702 and one user can use multiple computers 702.

Implementations of the subject matter and the functional operations described in this specification can be implemented in digital electronic circuitry, in tangibly embodied computer software or firmware, in computer hardware, including the structures disclosed in this specification and their structural equivalents, or in combinations of one or more of them. Software implementations of the described subject matter can be implemented as one or more computer programs. Each computer program can include one or more modules of computer program instructions encoded on a tangible, non-transitory, computer-readable computer-storage medium for execution by, or to control the operation of, data processing apparatus. Alternatively, or additionally, the program instructions can be encoded in/on an artificially generated propagated signal. For example, the signal can be a machine-generated electrical, optical, or electromagnetic signal that is generated to encode information for transmission to a suitable receiver apparatus for execution by a data processing apparatus. The computer-storage medium can be a machine-readable storage device, a machine-readable storage substrate, a random or serial access memory device, or a combination of computer-storage mediums.

The term "real-time," "real time," "realtime," "real (fast) time (RFT)," "near(ly) real-time (NRT)," "quasi real-time," or similar terms (as understood by one of ordinary skill in the art), means that an action and a response are temporally proximate such that an individual perceives the action and the response occurring substantially simultaneously. For example, the time difference for a response to display (or for an initiation of a display) of data following the individual's action to access and/or interact with the data can be less than 1 millisecond (ms), less than 1 second(s), or less than 5 s. While the requested data need not be displayed (or initiated for display) instantaneously, it is displayed (or initiated for display) without any intentional delay, taking into account processing limitations of a described computing system and time required to, for example, gather, accurately measure, analyze, process, store, or transmit the data.

The terms "data processing apparatus," "computer," and "electronic computer device" (or equivalent as understood by one of ordinary skill in the art) refer to data processing hardware. For example, a data processing apparatus can encompass all kinds of apparatuses, devices, and machines for processing data, including by way of example, a programmable processor, a computer, or multiple processors or computers. The apparatus can also include special purpose logic circuitry including, for example, a central processing unit (CPU), a field-programmable gate array (FPGA), or an application-specific integrated circuit (ASIC). In some implementations, the data processing apparatus or special purpose logic circuitry (or a combination of the data processing apparatus or special purpose logic circuitry) can be hardware- or software-based (or a combination of both hardware- and software-based). The apparatus can optionally include code that creates an execution environment for computer programs, for example, code that constitutes processor firmware, a protocol stack, a database management system, an operating system, or a combination of execution environments. The present disclosure contemplates the use of data processing apparatuses with or without conventional operating systems, such as LINUX, UNIX, WINDOWS, MAC OS, ANDROID, or IOS.

A computer program, which can also be referred to or described as a program, software, a software application, a module, a software module, a script, or code, can be written in any form of programming language. Programming languages can include, for example, compiled languages, interpreted languages, declarative languages, or procedural languages. Programs can be deployed in any form, including as stand-alone programs, modules, components, subroutines, or units for use in a computing environment. A computer program can, but need not, correspond to a file in a file system. A program can be stored in a portion of a file that holds other programs or data, for example, one or more scripts stored in a markup language document, in a single file dedicated to the program in question, or in multiple coordinated files storing one or more modules, sub-programs, or portions of code. A computer program can be deployed for execution on one computer or on multiple computers that are located, for example, at one site or distributed across multiple sites that are interconnected by a communication network. While portions of the programs illustrated in the various figures may be shown as individual modules that implement the various features and functionality through various objects, methods, or processes, the programs can instead include a number of sub-modules, third-party services, components, and libraries. Conversely, the features and functionality of various components can be combined into single components as appropriate. Thresholds used to make computational determinations can be statically, dynamically, or both statically and dynamically determined.

The methods, processes, or logic flows described in this specification can be performed by one or more programmable computers executing one or more computer programs to perform functions by operating on input data and generating output. The methods, processes, or logic flows can also be performed by, and apparatus can also be implemented as, special purpose logic circuitry, for example, a CPU, an FPGA, or an ASIC.

Computers suitable for the execution of a computer program can be based on one or more of general and special purpose microprocessors and other kinds of CPUs. The elements of a computer are a CPU for performing or executing instructions and one or more memory devices for storing instructions and data. Generally, a CPU can receive instructions and data from (and write data to) a memory.

Graphics processing units (GPUs) can also be used in combination with CPUs. The GPUs can provide specialized processing that occurs in parallel to processing performed by CPUs. The specialized processing can include artificial intelligence (AI) applications and processing, for example. GPUs can be used in GPU clusters or in multi-GPU computing.

A computer can include, or be operatively coupled to, one or more mass storage devices for storing data. In some implementations, a computer can receive data from, and transfer data to, the mass storage devices including, for example, magnetic, magneto-optical disks, or optical disks. Moreover, a computer can be embedded in another device, for example, a mobile telephone, a personal digital assistant (PDA), a mobile audio or video player, a game console, a global positioning system (GPS) receiver, or a portable storage device such as a universal serial bus (USB) flash drive.

Computer-readable media (transitory or non-transitory, as appropriate) suitable for storing computer program instructions and data can include all forms of permanent/non-permanent and volatile/non-volatile memory, media, and memory devices. Computer-readable media can include, for example, semiconductor memory devices such as random access memory (RAM), read-only memory (ROM), phase change memory (PRAM), static random access memory (SRAM), dynamic random access memory (DRAM), erasable programmable read-only memory (EPROM), electrically erasable programmable read-only memory (EEPROM), and flash memory devices. Computer-readable media can also include, for example, magnetic devices such as tape, cartridges, cassettes, and internal/removable disks. Computer-readable media can also include magneto-optical disks and optical memory devices and technologies including, for example, digital video disc (DVD), CD-ROM, DVD+/−R, DVD-RAM, DVD-ROM, HD-DVD, and BLU-RAY. The memory can store various objects or data, including caches, classes, frameworks, applications, modules, backup data, jobs, web pages, web page templates, data structures, database tables, repositories, and dynamic information. Types of objects and data stored in memory can include parameters, variables, algorithms, instructions, rules, constraints, and references. Additionally, the memory can include logs, policies, security or access data, and reporting files. The processor and the memory can be supplemented by, or incorporated into, special purpose logic circuitry.

Implementations of the subject matter described in the present disclosure can be implemented on a computer having a display device for providing interaction with a user, including displaying information to (and receiving input from) the user. Types of display devices can include, for example, a cathode ray tube (CRT), a liquid crystal display (LCD), a light-emitting diode (LED), and a plasma monitor. Display devices can include a keyboard and pointing devices including, for example, a mouse, a trackball, or a trackpad. User input can also be provided to the computer through the use of a touchscreen, such as a tablet computer surface with pressure sensitivity or a multi-touch screen using capacitive or electric sensing. Other kinds of devices can be used to provide for interaction with a user, including to receive user feedback including, for example, sensory feedback including visual feedback, auditory feedback, or tactile feedback. Input from the user can be received in the form of acoustic, speech, or tactile input. In addition, a computer can interact with a user by sending documents to, and receiving documents from, a device that the user uses. For example, the computer can send web pages to a web browser on a user's client device in response to requests received from the web browser.

The term "graphical user interface," or "GUI," can be used in the singular or the plural to describe one or more graphical user interfaces and each of the displays of a particular graphical user interface. Therefore, a GUI can represent any graphical user interface, including, but not limited to, a web browser, a touch-screen, or a command line interface (CLI) that processes information and efficiently presents the information results to the user. In general, a GUI can include a plurality of user interface (UI) elements, some or all associated with a web browser, such as interactive fields, pull-down lists, and buttons. These and other UI elements can be related to or represent the functions of the web browser.

Implementations of the subject matter described in this specification can be implemented in a computing system that includes a back-end component, for example, as a data server, or that includes a middleware component, for example, an application server. Moreover, the computing system can include a front-end component, for example, a client computer having one or both of a graphical user interface or a Web browser through which a user can interact with the computer. The components of the system can be interconnected by any form or medium of wireline or wireless digital data communication (or a combination of data communication) in a communication network. Examples of communication networks include a local area network (LAN), a radio access network (RAN), a metropolitan area network (MAN), a wide area network (WAN), Worldwide Interoperability for Microwave Access (WIMAX), a wireless local area network (WLAN) (for example, using 802.11 a/b/g/n or 802.20 or a combination of protocols), all or a portion of the Internet, or any other communication system or systems at one or more locations (or a combination of communication networks). The network can communicate with, for example, Internet Protocol (IP) packets, frame relay frames, asynchronous transfer mode (ATM) cells, voice, video, data, or a combination of communication types between network addresses.

The computing system can include clients and servers. A client and server can generally be remote from each other and can typically interact through a communication network. The relationship of client and server can arise by virtue of computer programs running on the respective computers and having a client-server relationship.

Cluster file systems can be any file system type accessible from multiple servers for read and update. Locking or consistency tracking may not be necessary since the locking of exchange file system can be done at the application layer. Furthermore, Unicode data files can be different from non-Unicode data files.

The disclosure includes a wearable ultrasound system that can include an ultrathin ultrasound device comprising an array of piezoelectric elements disposed on a backing layer and coupled to a flexible printed circuit board (FPCB); an adjustable patch attachable to a region of a subject, the adjustable patch operably holds the ultrathin ultrasound device therein so that the ultrathin ultrasound device is adjustably coupled to the region of the subject through coupling fluid in the adjustable patch; and a portable control system communicatively coupled to the ultrathin ultrasound device.

The disclosure includes a band system for affixing one or more wearable ultrasound transducer devices, the band system can include: one or more mounts, wherein each mount is defined by a horizontal plane and a longitudinal axis that is vertical to the horizontal plane, wherein each mount encloses a respective knob operable to rotate around the vertical axis and tilt about the horizontal plane; and straps tied to the one or more mounts, wherein the straps are adjustable to wrap around a subject so that the subject can wear the one or more mounts, wherein each mount houses a wearable ultrasound transducer device such that, by virtue of wearing the one or more mounts, each wearable ultrasound transducer device is placed with sufficient acoustic coupling to the subject's skin.

Configurable Wearable Ultrasound Band, e.g., for Continuous, Multi-View Imaging

The following detailed description explains a wearable system for strapping an ultrasound device assembly, which can include the ultrathin ultrasound device 100 of FIG. 1 or other components or elements described in this document, on a subject's body that enables hands-free, continuous, multi-angle, and multi-target imaging of internal targets. Various implementations can provide a modular, secure, and easily adjustable wearable ultrasound system that allows clinicians and patients to perform or receive imaging from multiple angles and at various anatomical locations without relying on operator skill during imaging. Examples of the wearable system can incorporate a wearable ultrasound band system including one or more mounts each coupled with an adjustable ball knob to which an ultra-thin ultrasonic transducer device can be attached. The ball knob is capable for controlling an orientation of the ultrasound device via rotational control and tilt control so that the transducer's emitting surface, as facing the subject's body, can be adjusted to accommodate the needs of various imaging applications. The wearable ultrasound band system also includes a strap-based fixation system for anatomical conformity and an integrated miniaturized control unit. The strap-based fixation system can include adjustable straps attached to the one or more mounts so that, under the force the straps, the mount assembly can be worn by the subject and positioned on a desired surface of the subject. For example, the adjustable straps can be tightened to induce a desired pressure on the surface of the human body as if the ultrasound transducer device is pressed against, for example, the chest of the subject for cardiac imaging.

The implementations provide adjustable wearing gear for an ultrathin ultrasonic transducer device. The ultrathin ultrasonic transducer device can have an overall thickness of less than 5 millimeters (mm), which renders the device lightweight, highly portable, and suitable for wearable applications. The design can reduce noise, enhance the quality of ultrasound imaging, and enable integration into a variety of medical and industrial applications that require compact ultrasound solutions. Additional details can be found in U.S. provisional applications 63/703,982, 63/703,984, and 63/703,985 filed on Oct. 6, 2024, all of which are incorporated by reference herein. The implementations generally include an adjustable mount to house the ultrathin ultrasound device. Examples of the adjustable mount can include a circular mount coupled with a ball knob assembly that allows the attached ultrasound transducer array to rotate and tilt relative to the skin surface. The ball-and-socket configuration permits multi-axis adjustment, supporting dynamic reorientation to accommodate various ultrasound windows without displacing the patient or repositioning the device manually.

Figure 8:
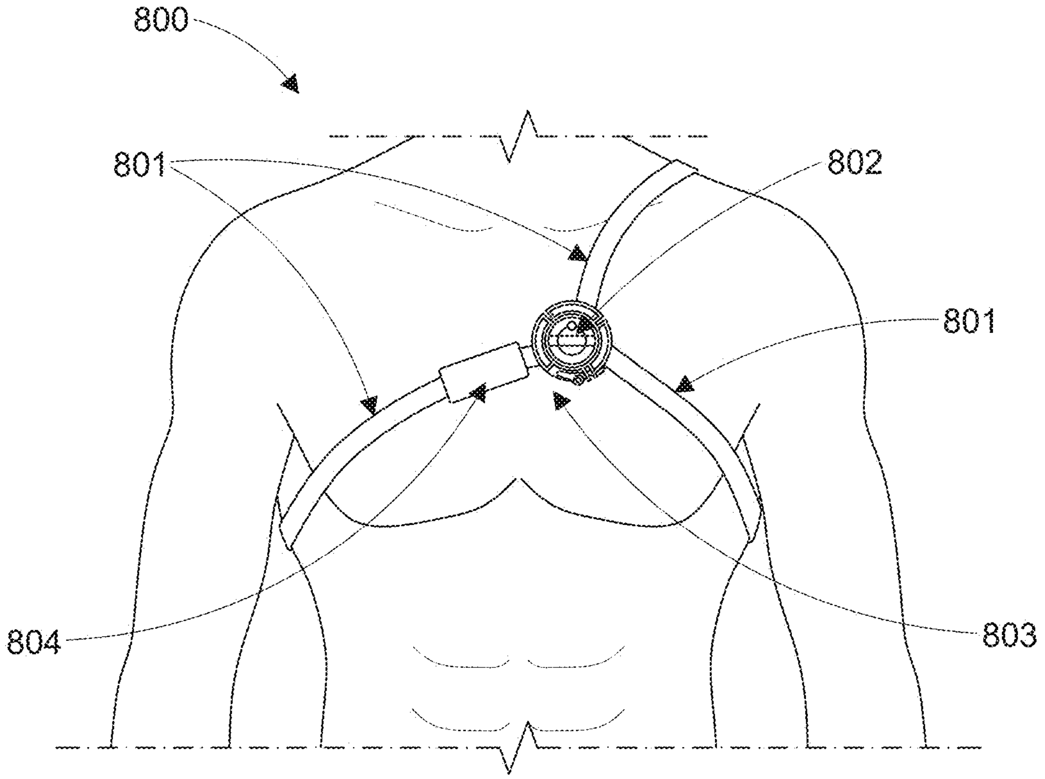
FIG. 8 illustrates an example of a wearable ultrasound band bound on a subject's body for continuous monitoring according to some implementations of the present disclosure.

FIG. 8 illustrates an example of a wearable ultrasound band 800 that can be worn on a subject's body for continuous monitoring using an ultrasound transducer device. As illustrated, band 800 includes straps 801 attached to mount 803 where a ball knob 802 is placed to form an assembly of mount 803 and ball knob 802. Straps 801 can include multiple stems (e.g., three) that can be adjusted to affix an ultrasound transducer array to the patient's body, which allows for secure fixation with controllable tension across diverse anatomical contours.

The strap framework is composed of skin-friendly materials to ensure patient comfort and reduce skin irritation. Integrated support frames are used to distribute mechanical load evenly, minimizing motion artifacts caused by respiration, movement, or posture changes during extended wear. The strap system may incorporate modular attachment features such as snap-in slots, hook-and-loop fasteners, and ratcheting tensioners for precise mechanical alignment. In some implementations, the wearable system includes peel-and-stick straps that provide secure yet easily removable fixation. These straps can be repositioned or replaced during long-term use without compromising comfort or performance. In various implementations, the overall design prioritizes both patient comfort and clinician configurability, thus rendering the device suitable for continuous use in settings ranging from ambulatory care to intensive care units and remote home monitoring.

By way of example, straps 801, when tightened, operate to affix the assembly of mount 803 and ball knob 802 to a desired position on the skin of the subject. For cardiac imaging and monitoring, the desired position can be an intercostal space on the chest through which ultrasound can be emitted to insonify the cardiac cavity. The wearable ultrasound band system is capable for on various anatomical sites, including but not limited to the chest, abdomen, flanks, and lower pelvis. This flexibility enables imaging of a variety of targets such as the heart, lungs, liver, kidneys, bladder, stomach, and fetal structures.

An ultra-thin ultrasound transducer device can be secured in an assembly of mount 803 and ball knob 802. Detailed examples can be found in U.S. provisional applications 63/703,982, 63/703,984, and 63/703,985 filed on Oct. 6, 2024, all of which are incorporated by reference herein. The ultrasound transducer device can be connected to a miniaturized ultrasound control system that controls the activation of each transducer element for transmitting pulses of ultrasound into the subject and for receiving back-scattered ultrasound signals for pulse-echo imaging.

Figure 9:
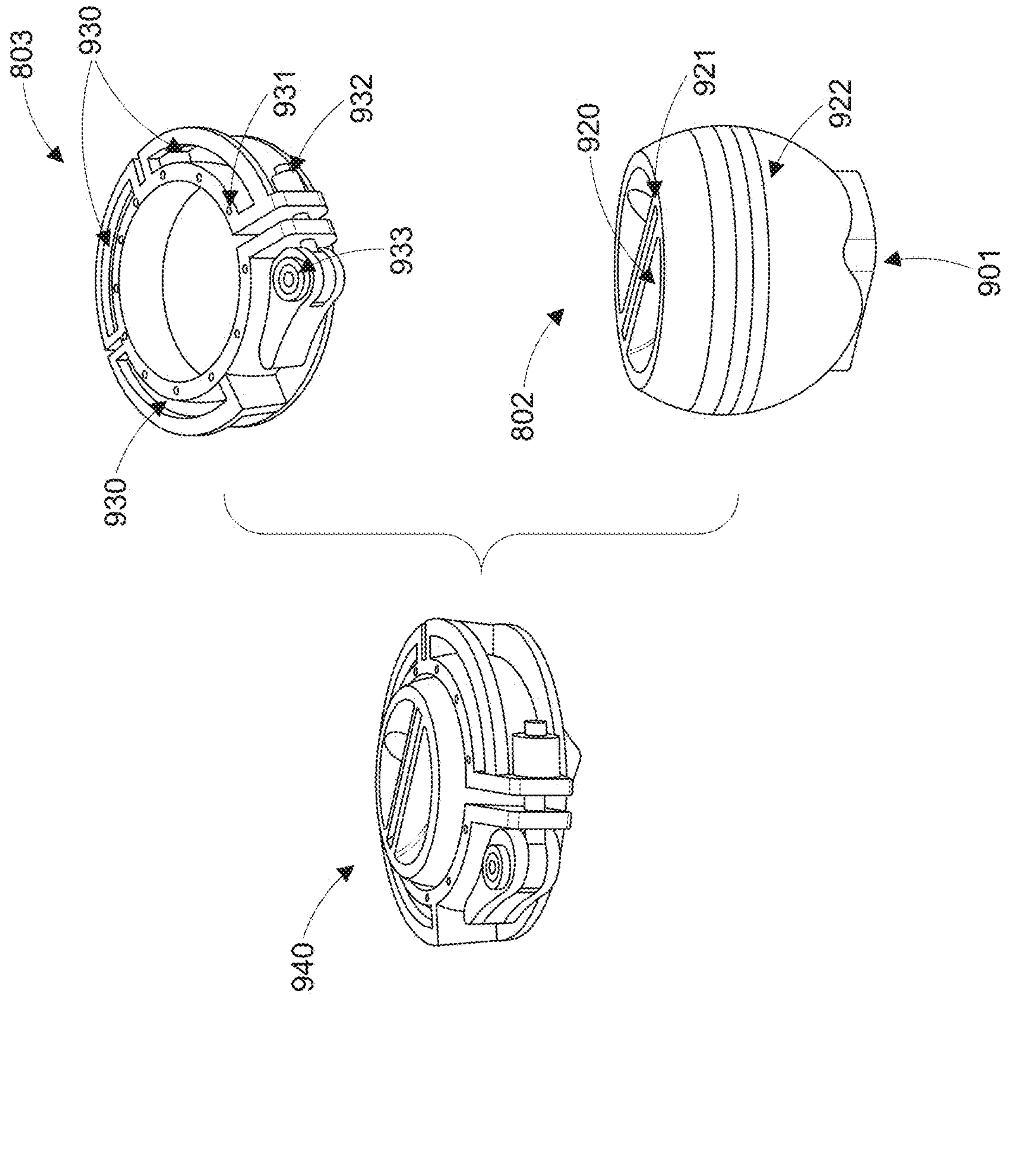
FIG. 9 illustrates a schematic and perspective view for an example of a circular mount and a ball knob according to some implementations of the present disclosure.

Further referring to FIG. 9, an assembly example 940 includes mount 803 (e.g., circular mount) coupled with a ball knob 802 that allows the attached ultrasound transducer array to rotate and tilt relative to the skin surface. As illustrated, circular mount 803 includes support frames 930, rotation scale 931, tension adjustable nut 932, and locker 933. In more detail, the support frames 930 accommodate each strap. Rotating scale 931 includes a rotation scale with twelve (12) calibrated marks at 30-degree intervals. Tension adjustable nut 932 is placed on the circumference of support frames 930 and can be tightened or loosened to adjust tension on the straps. Locker 933 is positioned on the side of support frames 930 and can be pressed to lock the circular mount from further rotation (or released to unlock).

As illustrated in FIG. 9, ball knob 802 includes grooves 920, marker 921, and tilting scale 922. Ultrasound transducer array 901 is housed on the bottom of ball knob 802 to face the subject's skin. As illustrated, grooves 920 are arranged for control by, for example, operator fingers. Using tactile engagement, manual fine-tuning of the orientation can be accomplished without using auxiliary tools. Tilting scale 922 provides three calibrated marks at 10-degree intervals. These angular markings enable reproducible positioning of the ultrasound transducer array 901 during longitudinal studies or serial imaging sessions. An orientation marker 921 is also integrated on the ball knob 802 to assist clinicians in aligning the ultrasound transducer array 901 with standard anatomical planes. Once aligned, a tension-adjustable nut 932 and locking mechanism of locker 933 secure the ultrasound transducer array 901 in the desired position with controllable pressure to ensure consistent skin contact and acoustic coupling.

In sum, the wearable band system has a core structure including a circular mount 803 and a ball knob 802 to allow the ultrasound transducer array 901 to be rotated (e.g., in-plane) and tilted (e.g., azimuthal) to different angles. For example, the ball-and-socket configuration permits multi-axis adjustment, support dynamic reorientation to accommodate various ultrasound windows without displacing the patient or repositioning the device manually.

The assembly of circular mount and ball knob can accommodate a variety of ultrasound transducer modules, including phased, linear, curved, and matrix array formats. In some implementations, a miniaturized ultrasound control system is embedded directly within the ball knob or mount housing. This compact module may include signal drivers (e.g., amplifiers, buffers), analog front-end electronics (e.g., matching and tuning elements, analog to digital converters (ADC)), digital processing units (e.g., digital signal processing (DSP) modules, digital beamforming modules), batteries, and wireless communication modules for real-time data transmission to external devices such as phones, tablets, or bedside monitors. Here, the beamforming modules can apply to both the transmission control (i.e., transmission focusing control) and the receiving control (i.e., operating on backscattered ultrasound signals). In other implementations, miniature actuators or motors may be integrated into the knob or mount structure to enable remote control of rotation and tilting, allowing clinicians or automated algorithms to adjust imaging angles without physical contact with the device. In some cases, actuators can include one or more ball-and-socket joints or other couplings, such as joints or hinges. Actuators can be used to direct ultrasound emanating from a wearable ultrasound device, e.g., including one or more ultrasound transducers. A mount, e.g., using one or more actuators, can allow an ultrasound transducer array to be adjusted, e.g., moved, rotated, tilted, or pressed, such as in a way that can be similar to movement by a sonographer. Adjustments can help improve ultrasound imaging, e.g., while the device is worn on a body.

The electrical connection between the ultrasound transducer array 901 and the control system 804 may be implemented using flexible printed circuits (FPCs), embedded micro-coaxial cables, or direct chip integration, depending on the transducer's configuration and spatial constraints. The control system 804 may also include power routing to embedded motors for position adjustment. Additionally, the transducer 901 may interface with a cloud-based or edge-deployed AI-enabled image processing platform for real-time image reconstruction, quality assessment, segmentation, and diagnostic support. This integration allows for autonomous imaging workflows, reducing the burden on skilled personnel and enabling scalable deployment in both clinical and at-home settings.

Figures 10A, 10B, 10C, 10D, 10E, 10F, 10G, 10H, 10I:
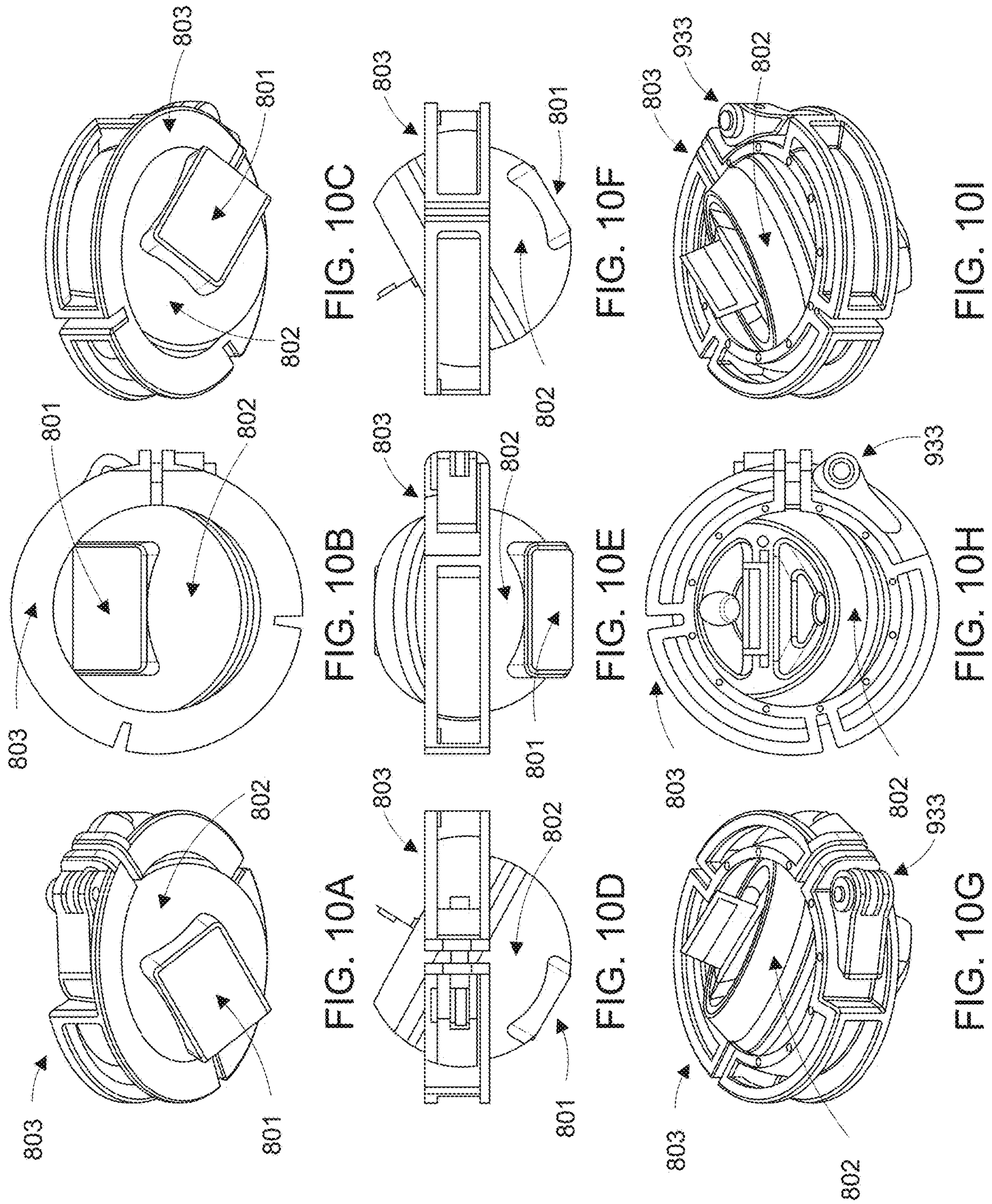
FIGS. 10A to 10I respectively show various perspective views and side views of an assembly of the circular mount and the ball knob of FIG. 9 with the ball knob arranged in various rotation and tiling positions.

FIGS. 10A to 10I respectively show various perspective views and side views of an assembly of the circular mount 803 and the ball knob 802 of FIG. 9 with the ball knob arranged in various rotation and tiling positions. FIGS. 10A to 10C represent perspective views from the lower side of the ball knob 802 where ultrasound transducer array 901 is housed. These perspective views illustrate that ball knob 802 is engaged within the circular mount 803 and the ultrasound transducer array 901 is positioned to face the human skin. FIGS. 10D to 10F represent perspective views from the lateral side of the circular mount 803 with the ultrasound transducer array 901 positioned to face the human skin. FIGS. 10G to 10I represent perspective views from the upper side of the ball knob 802 revealing various structures on the circular mount 803 such as locker 933.

Figure 11B:
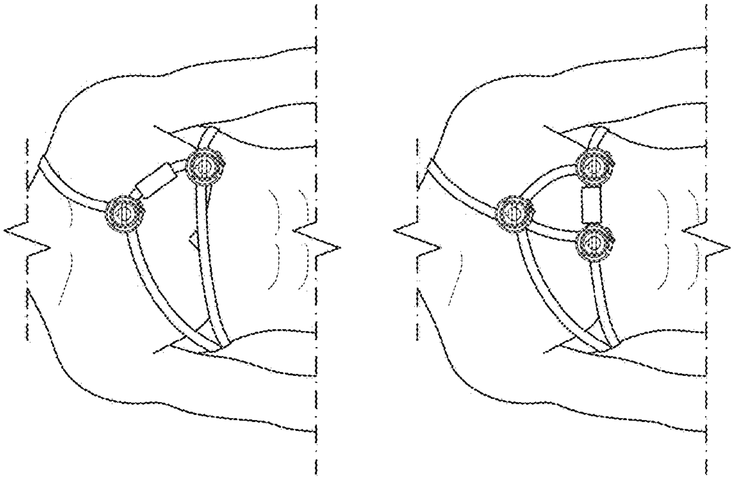
FIGS. 11A to 11E illustrate examples for configuring the wearable ultrasound band according to some implementations of the present disclosure.
Figure 11A:
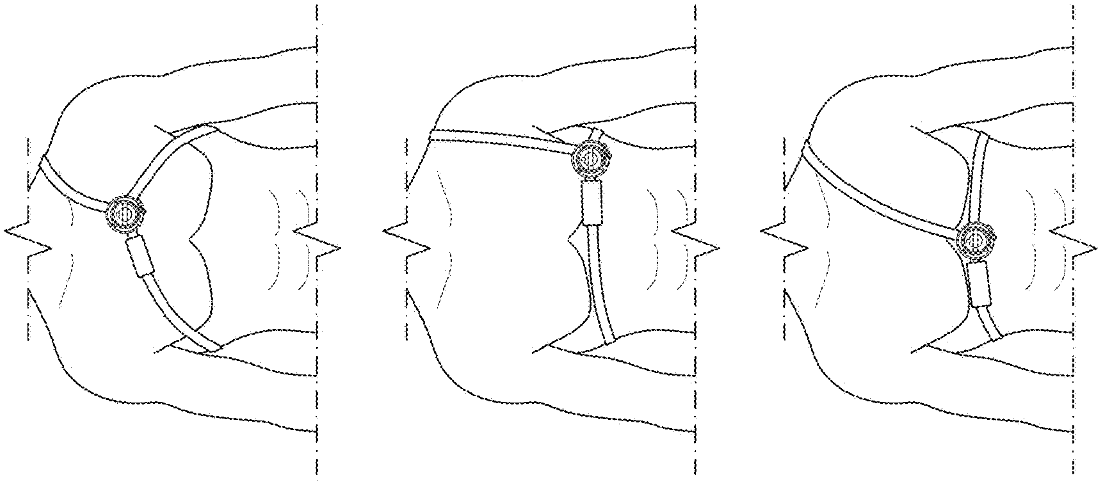
Figure 11C:
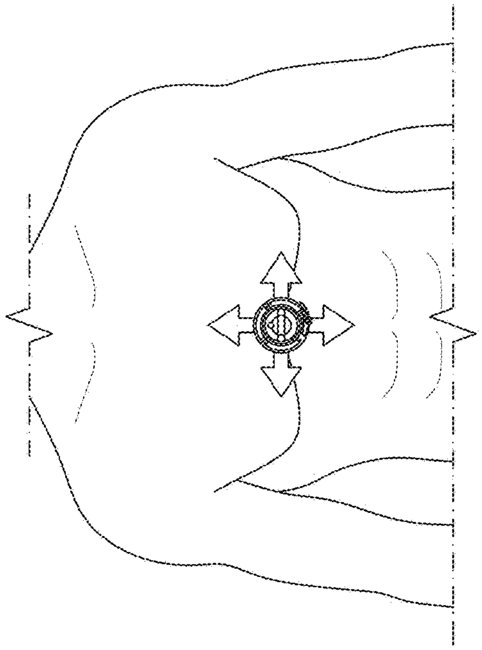
Figure 11D:
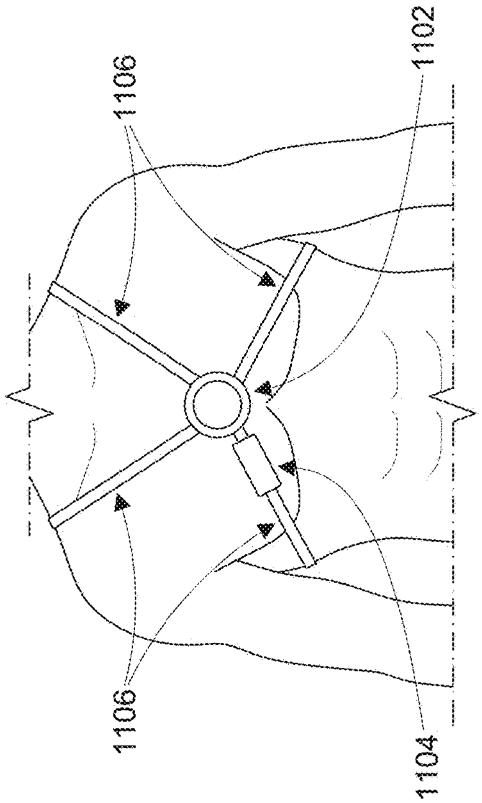

FIGS. 11A to 11E illustrate examples for configuring the wearable ultrasound band according to some implementations of the present disclosure. FIG. 11A shows three configurations for the wearable ultrasound band system providing, respectively, the parasternal view, the apical view, and the subcostal view for cardiac imaging. While FIG. 11A illustrates examples of providing a single view using the wearable ultrasound band system, the wearable ultrasound system can include multiple bands for positioning multiple transducer modules in wearable configurations for simultaneous for multi-site imaging. FIG. 11B provides examples of using multiple bands to generate two views (namely, parasternal and apical views) and three views (namely, parasternal, apical, and subcostal views). In these examples, multiple wearable ultra-thin ultrasound transducers arrays can operate from each respective view to generate pulse-echo data, which, when used to generate images, provide 2D images from the respective views (e.g., parasternal view and apical views orthogonal to each other). These 2D images can be consolidated to reconstruct a composite anatomical model or to simultaneously monitor dynamic physiological processes. FIG. 11C is a general diagram showing the wearable ultrasound band system can reposition the ultra-thin ultrasound transducer array, e.g., along tracks provided by the bands, to any desired position on the skin of the subject. FIG. 11D shows an example of the wearable ultrasound band system including an ultrasound transducer module 1102 secured by four bands 1106 that wrap around the subject's torso. In the example of FIG. 11D, two of the four bands are strapped around the shoulders, while the other two of the four bands are strapped around the chest. This example may distribute the tightening forces evenly on both lateral sides of the torso to secure a desired positioning of the ultrasound transducer module 1102. The wearable ultrasound band system can also include a control system 1104 with user interface elements (e.g., push buttons, adjustment knobs) to allow a user to control, e.g., the mechanical placement of the bands 1006, or an electronic configuration of ultrasound transducer module 1102.

Figure 11E:
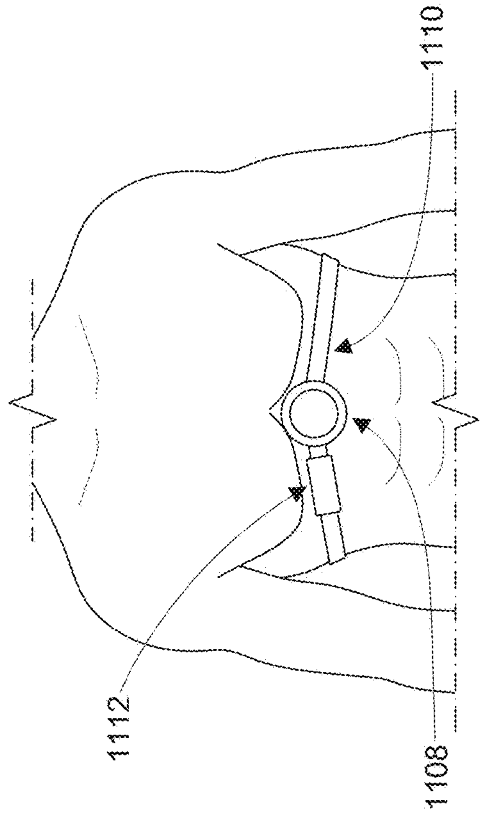

FIG. 11E shows an example of the wearable ultrasound band system including an ultrasound transducer module 1108 secured by a strap 1110 that wraps around the subject's torso, e.g., tightened laterally. This example reduces the number of straps used compared to other examples, such as FIG. 11D. In some cases, a subject may experience discomfort caused by straps. Using fewer straps may reduce any potential discomfort, e.g., caused by straps rubbing or pressing into the skin. The wearable ultrasound band system can include a control system 1112 with one or more user interface elements (e.g., push buttons, adjustment knobs) to allow a user to control, e.g., the mechanical placement of the strap 1110, or an electronic configuration of ultrasound transducer module 1108. The ultrasound transducer module 1108 can be enclosed in a suitable housing, such as a plastic case or encasing made of a suitable material. One or more straps can be used to attach a wearable ultrasound band system to various parts of a human or animal body. Body parts can include at least one of a torso, head, neck, or limbs.

While this specification contains many specific implementation details, these should not be construed as limitations on the scope of what may be claimed, but rather as descriptions of features that may be specific to particular implementations. Certain features that are described in this specification in the context of separate implementations can also be implemented, in combination, in a single implementation. Conversely, various features that are described in the context of a single implementation can also be implemented in multiple implementations, separately, or in any suitable sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking or parallel processing (or a combination of multitasking and parallel processing) may be advantageous and performed as deemed appropriate.

Moreover, the separation or integration of various system modules and components in the previously described implementations should not be understood as requiring such separation or integration in all implementations. It should be understood that the described program components and systems can generally be integrated together in a single software product or packaged into multiple software products.

Accordingly, the previously described example implementations do not define or constrain the present disclosure. Other changes, substitutions, and alterations are also possible without departing from the spirit and scope of the present disclosure.

Furthermore, any claimed implementation is considered to be applicable to at least a computer-implemented method; a non-transitory, computer-readable medium storing computer-readable instructions to perform the computer-implemented method; and a computer system including a computer memory interoperably coupled with a hardware processor configured to perform the computer-implemented method or the instructions stored on the non-transitory, computer-readable medium.

The following are non-limiting examples of various embodiments of the present disclosure.

A-1. An adjustable patch, comprising:

a mounting plate integrated with a gel sprue, the mounting plate sized and shaped to hold an ultrasonic transducer array, the gel sprue constructed to allow replenishment of coupling gel for the ultrasonic transducer array; and an adjustment base disposed underneath the mounting plate, the adjustment base including a clip configured to grip the mounting plate, wherein the clip is the coupled with an adjustment knob operable to tighten or loosen the clip so that the ultrasonic transducer array can be securely attached to, or detached from, a subject's skin, wherein the adjustable patch is attachable to the subject's skin using one or more breathable medical tapes.

A-2. The adjustable patch of claim A-1, wherein the mounting plate comprises an external connection configured to connect the ultrasonic transducer array to a portable control system so that the ultrasonic transducer array is under the control of the portable control system.

A-3. The adjustable patch of claim A-1, wherein the mounting plate is operable to accommodate changing an orientation of the ultrasonic transducer relative to the subject's skin for improved ultrasound imaging.

A-4. The adjustable patch of claim A-1, wherein the mounting plate is morphable to adapt to multiple types of ultrasonic transducer arrays.

A-5. The adjustable patch of claim A-1, wherein the mounting plate is resizable to accommodate variations in a subject's body type or size.

B-1. An ultrathin ultrasound device, comprising:

an ultrasonic transducer array that includes a plurality of elements each comprising a back electrode and a front electrode, and each configured to:

generate ultrasound waves for launching from a front surface into a region of a subject, and receive echoes from the region in response to the ultrasound waves being launched from the front surface, the front surface encompassing the front electrode;

a backing layer positioned at a back surface of the ultrasonic transducer array and configured to absorb the ultrasound waves generated by the ultrasonic transducer array that otherwise would be launched from the back surface, the back surface encompassing the back electrode; and a flexible printed circuit board (FPCB) electrically connected to the front electrode and the back electrode of each of the plurality of elements of the ultrasonic transducer array so that the plurality of elements can generate the ultrasound waves when driven by electrical pulses and generate electrical signals when the echoes are received, wherein the ultrathin ultrasound device is sized at five millimeters or less in thickness.

B-2. The ultrathin ultrasound device of claim B-1, wherein the plurality of elements comprise piezoelectric materials made from at least one of: a single crystal, a composite, or a lead zirconate titanate.

B-3. The ultrathin ultrasound device of claim B-1, wherein the plurality of elements comprise at least one of: a capacitive micromachined transducer (CMUT) or a piezoelectric micromachined transducer (PMUT).

B-4. The ultrathin ultrasound device of claim B-1, further comprising:

at least one acoustic lens disposed over the front surface of each element of the ultrasonic transducer array and shaped to focus the ultrasound waves being launched and the echoes being received in response thereto.

B-5. The ultrathin ultrasound device of claim B-4, further comprising:

one or more matching layers disposed between the front surface of each element of the ultrasonic transducer array and the at least one acoustic lens, wherein the one or more matching layers are characterized by an acoustic impedance that is in between that of each element of the ultrasonic transducer array and that of the at least one acoustic lens.

B-6. The ultrathin ultrasound device of claim B-5, wherein a thickness of the one or more matching layers is a quarter of a length of a wave of which the ultrasonic transducer array is configured to generate.

B-7. The ultrathin ultrasound device of claim B-1, wherein the FPCB is electrically connected to one electrode of each element of the ultrasonic transducer array using at least one of: conductive epoxy bonding or soldering, and wherein the FPCB is electrically connected to the other electrode of each element of the ultrasonic transducer array using wire bonding.

B-8. The ultrathin ultrasound device of claim B-1, wherein the backing layer is made from an epoxy resin mixed with a high-density metal or a ceramic-based material.

B-9. The ultrathin ultrasound device of claim B-8, wherein the epoxy resin is mixed with one or more of a tungsten powder, a silver powder, an alumina powder, or a carbon fiber.

B-10. The ultrathin ultrasound device of claim B-1, wherein the backing layer is made from one or more metamaterials.

C-1. A wearable ultrasound system comprising:

an ultrathin ultrasound device comprising an array of piezoelectric elements disposed on a backing layer and coupled to a flexible printed circuit board (FPCB);

an adjustable patch attachable to a region of a subject, the adjustable patch operably holds the ultrathin ultrasound device therein so that the ultrathin ultrasound device is adjustably coupled to the region of the subject through coupling fluid in the adjustable patch; and a portable control system communicatively coupled to the ultrathin ultrasound device, the portable control system comprising one or more circuits configured to:

control the ultrathin ultrasound device to emit ultrasound waves into the region of the subject, and receive echoes from the region of the subject in response to the ultrasound waves;

receive electrical signals from the ultrathin ultrasound device in response to the ultrathin ultrasound device receiving the echoes from the region of the subject; and generate one or more ultrasound images or waveform signals based on the electrical signals.

C-2. The wearable ultrasound system of claim C-1, wherein the portable control system further comprises: a rechargeable battery module.

C-3. The wearable ultrasound system of claim C-2, wherein the one or more circuits comprise a primary circuit board and a secondary circuit board.

C-4. The wearable ultrasound system of claim C-3, wherein the primary circuit board comprises one or more beamforming circuit configured to:

adaptively control a focal depth of each transmission event of the ultrathin ultrasound device to insonify a region inside the subject, and dynamically generate one or more receive beams based on echo signals in response to each transmission event.

C-5. The wearable ultrasound system of claim C-3, wherein the primary circuit board comprises at least one of: a field programmable gated array (FPGA), a graphic processing unit (GPU), or an application specific integrated circuit (ASIC).

C-6. The wearable ultrasound system of claim C-3, wherein the secondary circuit board comprises a power management module managing at least one of: charging of the rechargeable battery, regulating a voltage being supplied to the primary circuit board or the ultrathin ultrasound device, and negotiating a power being distributed to the primary circuit board or the ultrathin ultrasound device.

C-7. The wearable ultrasound system of claim C-1, wherein the portable control system is connected to the ultrathin ultrasound device via a cable or flexible printed circuit (FPC) over which the portable control system operates the ultrathin ultrasound device and receives the electrical signals.

C-8. The wearable ultrasound system of claim C-7, wherein the cable or FPC is wired to the flexible printed circuit board (FPCB).

C-9. The wearable ultrasound system of claim C-1, wherein the portable control system is wirelessly connected to the ultrathin ultrasound device so that the portable control system wirelessly operates the ultrathin ultrasound device for each transmission event and wirelessly receives the electrical signals resulting from each transmission event.

C-10. The wearable ultrasound system of claim C-1, wherein the portable control system is wirelessly connected to one or more external devices so that the one or more ultrasound images are streamed to the one or more external devices for real-time display.

C-11. A method to operate a wearable ultrasound system, the method comprising:

assembling a wearable ultrasound patch that includes:

an ultrathin ultrasound device comprising an array of piezoelectric elements disposed on a backing layer and coupled to a flexible printed circuit board (FPCB); and an adjustable patch attachable to a region of a subject, the adjustable patch operably holds the ultrathin ultrasound device therein; and affixing the wearable ultrasound patch on the region of the subject using medical tapes of the adjustable patch so that the ultrathin ultrasound device is adjustably coupled to the region of the subject through coupling fluid held in the adjustable patch; and operating a portable control system communicatively coupled to the ultrathin ultrasound device, wherein the portable control system is activated to:

control the ultrathin ultrasound device to emit ultrasound waves into the region of the subject, and receive echoes from the region of the subject in response to the ultrasound waves;

receive electrical signals from the ultrathin ultrasound device in response to the ultrathin ultrasound device receiving the echoes from the region of the subject; and generate one or more ultrasound images or waveform signals based on the electrical signals.

D-1. A band system for affixing one or more wearable ultrasound devices, the band system comprising:

one or more mounts, wherein each mount is defined by a horizontal plane and a longitudinal axis that is vertical to the horizontal plane, wherein each mount encloses a respective knob operable to rotate around the longitudinal axis and tilt about the horizontal plane; and straps tied to the one or more mounts, wherein the straps are adjustable to wrap around a subject so that the subject can wear the one or more mounts, wherein each mount houses a wearable ultrasound device such that, by virtue of wearing the one or more mounts, each wearable ultrasound device is placed with sufficient acoustic coupling with the subject's skin.

D-2. The band system of claim D-1, further comprising one or more actuating devices arranged on a mount of the one or more mounts or a knob of the one or more respective knobs, wherein the one or more actuating devices are configured to rotate the knob around the longitudinal axis and tilt the knob about the horizontal plane.

D-3. The band system of claim D-2, wherein the one or more actuating devices are configured to control a direction of ultrasound emanating from the wearable ultrasound device by at least one of the rotation of the knob or the tilting of the knob.

D-4. The band system of claim D-1, wherein at least one wearable ultrasound device is sized and shaped for attachment to a corresponding knob.

D-5. The band system of claim D-4, wherein at least one wearable ultrasound device, when placed in sufficient contact with the subject's skin, provides a separate view of an internal region of the subject.

D-6. The band system of claim D-5, wherein the internal region comprises at least one of: a heart region, an abdominal region, a neck region, a joint region, an extremity region, a lung region, and a head region.

D-7. The band system of claim D-5, wherein a composite view of the internal region is generated based on the separate views from respective wearable ultrasound devices.

D-8. The band system of claim D-5, wherein at least one wearable ultrasound device is coupled to a control system configured to drive the at least one wearable ultrasound device for imaging the internal region of the subject.

D-9. The band system of claim D-8, wherein the control system comprises at least one of: a matching and tuning element, an amplifier circuit, and a beamformer.

D-10. The band system of claim D-8, further comprising:

an electrical interface connecting an ultrasound device of the one or more wearable ultrasound devices to the control system.

D-11. The band system of claim D-8, wherein the control system has a form factor sufficiently small for fitting on a mount or a knob.

D-12. The band system of claim D-1, further comprising:

a locking mechanism on each mount and operable to lock the respective knob enclosed therein so that an orientation of an ultrasound device of the one or more wearable ultrasound devices with respect to the subject's skin is fixed.

D-13. The band system of claim D-12, wherein the locking mechanism comprises:

a nut coupled to a mount of the one or more mounts for regulating tension on the straps tied to the mount; and a latch togglable between a first position to fix an orientation of a respective knob, and a second position release the orientation of the knob.

D-14. The band system of claim D-1, wherein a mount of the one or more mounts and at least one strap of the straps are composed of biocompatible materials designed for prolonged skin contact and comfort.

D-15. The band system of claim D-1, wherein an ultrasound device of the one or more wearable ultrasound devices housed within a mount comprises one of: a phased array, a linear array, a curved array, a matrix array, or a reconfigurable array.

D-16. The band system of claim D-1, wherein each mount is embedded with markings to respectively indicate a degree of rotation and an angle for tilt.

D-17. The band system of claim D-16, wherein the markings are provided in a first number of intervals for rotational degrees and a second number of intervals for tilting angles.

What is claimed is:

1. An adjustable patch, comprising:

a mounting plate integrated with a gel sprue, the mounting plate sized and shaped to hold an ultrasonic transducer array, the gel sprue constructed to allow replenishment of coupling gel for the ultrasonic transducer array; and an adjustment base disposed underneath the mounting plate, the adjustment base including a clip configured to grip the mounting plate, wherein the clip is the coupled with an adjustment knob operable to tighten or loosen the clip so that the ultrasonic transducer array can be securely attached to, or detached from, a subject's skin, wherein the adjustable patch is attachable to the subject's skin using one or more breathable medical tapes.

2. The adjustable patch of claim 1, wherein the mounting plate comprises an external connection configured to connect the ultrasonic transducer array to a portable control system so that the ultrasonic transducer array is under the control of the portable control system.

3. The adjustable patch of claim 1, wherein the mounting plate is operable to accommodate changing an orientation of the ultrasonic transducer relative to the subject's skin for improved ultrasound imaging.

4. The adjustable patch of claim 1, wherein the mounting plate is morphable to adapt to multiple types of ultrasonic transducer arrays.

5. The adjustable patch of claim 1, wherein the mounting plate is resizable to accommodate variations in a subject's body type or size.

* * * * *